(12) United States Patent
Choura

(10) Patent No.: US 11,322,241 B2
(45) Date of Patent: May 3, 2022

(54) ELECTRONIC METHODS AND SYSTEMS FOR PROCESSING INFORMATION RELATED TO INTAKE OF SUPPLEMENTS BY A USER

(71) Applicant: Nonstop Evolving Corp., La Jolla, CA (US)

(72) Inventor: Sami Choura, San Diego, CA (US)

(73) Assignee: Nonstop Evolving Corp., La Jolla, CA (US)

( * ) Notice: Subject to any disclaimer, the term of this patent is extended or adjusted under 35 U.S.C. 154(b) by 0 days.

(21) Appl. No.: 16/932,759

(22) Filed: Jul. 18, 2020

(65) Prior Publication Data

US 2022/0020472 A1     Jan. 20, 2022

(51) Int. Cl.

| | |
|---|---|
| *G16H 20/60* | (2018.01) |
| *G16H 50/20* | (2018.01) |
| *G06Q 30/06* | (2012.01) |
| *G16H 40/67* | (2018.01) |
| *G06Q 50/00* | (2012.01) |
| *G06Q 10/10* | (2012.01) |
| *G06Q 30/02* | (2012.01) |
| *G06Q 10/08* | (2012.01) |
| *G06F 16/23* | (2019.01) |
| *G16H 10/60* | (2018.01) |

(Continued)

(52) U.S. Cl.
CPC ......... *G16H 20/60* (2018.01); *G06F 16/2379* (2019.01); *G06Q 10/087* (2013.01); *G06Q 10/109* (2013.01); *G06Q 30/0215* (2013.01); *G06Q 30/0605* (2013.01); *G06Q 30/0627* (2013.01); *G06Q 30/0629* (2013.01); *G06Q 30/0631* (2013.01); *G06Q 50/01* (2013.01); *G16H 10/60* (2018.01); *G16H 40/67* (2018.01); *G16H 50/20* (2018.01); *A61B 5/117* (2013.01); *A61B 5/4866* (2013.01)

(58) Field of Classification Search
CPC ........ G09B 19/0092; G09B 5/00; G09B 5/02; G16H 20/60
See application file for complete search history.

(56) References Cited

U.S. PATENT DOCUMENTS

| | | |
|---|---|---|
| 6,796,507 B2 | 9/2004 | Bean |
| 9,728,102 B2 | 8/2017 | Nusbaum |
| 10,614,724 B2 | 4/2020 | Catani |

(Continued)

*Primary Examiner* — Peter R Egloff
(74) *Attorney, Agent, or Firm* — Kanika Radhakrishnan; Evergreen Valley Law Group

(57) ABSTRACT

Embodiments provide systems and methods for processing information related to nutrient intake of a user associated with a user device. The method performed by a server system includes receiving a request to register the user with the server system through a health application installed on the user device. The method includes extracting user information from one or more sources and creating a user profile based on the user information. The method includes determining at least one nutrient for recommending to the user. The at least one nutrient is determined based on the user information. Further, the method includes comparing two or more products including the at least one nutrient. The method further includes facilitating a display of the comparison of at least a quantity of each ingredient in the two or more products on the health application installed on the user device.

19 Claims, 17 Drawing Sheets

(51) Int. Cl.
*A61B 5/00* (2006.01)
*A61B 5/117* (2016.01)

(56) References Cited

U.S. PATENT DOCUMENTS

| | | | | |
|---|---|---|---|---|
| 2009/0191514 | A1* | 7/2009 | Barnow | G16H 10/65 |
| | | | | 434/127 |
| 2013/0216982 | A1* | 8/2013 | Bennett | A61B 5/4866 |
| | | | | 434/127 |
| 2014/0106313 | A1* | 4/2014 | Steele | G09B 19/0092 |
| | | | | 434/127 |
| 2016/0103910 | A1* | 4/2016 | Kim | G16H 20/60 |
| | | | | 707/738 |
| 2016/0379520 | A1* | 12/2016 | Borel | G09B 19/0092 |
| | | | | 434/127 |
| 2017/0098056 | A1 | 4/2017 | Reddy | |
| 2017/0316488 | A1* | 11/2017 | Kremen | G09B 19/0092 |
| 2018/0053440 | A1* | 2/2018 | Staveley | G09B 19/0092 |
| 2019/0105551 | A1* | 4/2019 | Ray | A63B 22/02 |
| 2019/0172575 | A1* | 6/2019 | Reddy | G16H 40/63 |
| 2019/0362826 | A1 | 11/2019 | Viskovich | |

\* cited by examiner

ELECTRONIC METHODS AND SYSTEMS FOR PROCESSING INFORMATION RELATED TO INTAKE OF SUPPLEMENTS BY A USER

TECHNICAL FIELD

The present disclosure relates to information processing and, more particularly to, electronic techniques for processing different kinds of information for managing intake of micronutrients by a user.

BACKGROUND

In today's fast-paced life, most people are unable to pay attention to their diets. People tend to eat junk food, skip meals, and have unbalanced diets which results in their diets being devoid of essential nutrients like vitamins and minerals. Various dietary supplements are available in the market which contain essential nutrients and micronutrients.

However, it has been observed that these supplements may not benefit a person if not taken according to a proper schedule or in appropriate quantities. Further, the requirement of the dietary supplements in the body changes with time. The quantities of supplements differ for each individual based on his/her lifestyle. Further, due to a busy schedule, it may be difficult for an individual to track the intake of the supplements.

Moreover, the market is flooded with different products of dietary supplements. This may confuse a person to choose the right product suitable for his body and eventually, the person may end up choosing an inappropriate product. Additionally, the person may need to compare a lot of different products available which is a time consuming and frustrating process.

Therefore, there is a need for methods and systems for addressing the above-mentioned problems relating to the management of intake of dietary supplements.

SUMMARY

Various embodiments of the present disclosure provide systems and methods for managing nutrient intake of a user associated with a user device.

In an embodiment, a method for managing nutrient intake of a user associated with a user device is disclosed. The method performed by a server system includes receiving a request to register the user with the server system through a health application installed on the user device. The method includes extracting user information from one or more sources and creating a user profile based on the user information. The method includes determining at least one nutrient for recommending to the user. The at least one nutrient is determined based on the user information. Further, the method includes comparing two or more products including the at least one nutrient. The method further includes facilitating a display of the comparison of at least a quantity of each ingredient in the two or more products on the health application installed on the user device.

In another embodiment, a server system for managing nutrient intake of a user associated with a user device is disclosed. The server system has a memory and a processor. The memory is configured to store instructions. The processor is configured to execute the instructions stored in the memory and thereby cause the server system to at least perform receiving a request to register the user with the server system through a health application installed on the user device. The server system is caused to extract user information from one or more sources and create a user profile based on the user information. The server system is caused to determine at least one nutrient for recommending to the user. The at least one nutrient is determined based on the user information. Further, the server system is caused to compare two or more products including the at least one nutrient. The server system is further caused to facilitate a display of the comparison of at least a quantity of each ingredient in the two or more products on the health application installed on the user device.

In yet another embodiment, a server system for managing nutrient intake of a user associated with a user device is disclosed. The server system includes a memory and a processor. The memory is configured to store instructions. The processor is configured to execute the instructions stored in the memory and thereby cause the system to perform at least receiving a request to register the user with the server system through a health application installed on the user device. The server system is caused to extract user information from one or more sources and create a user profile based on the user information. The server system is caused to determine at least one nutrient for recommending to the user. The at least one nutrient is determined based on the user information. The server system is caused to determine one or more products from a plurality of products. The one or more products are determined based on the determination of the at least one nutrient. Further, the server system is caused to facilitate display of the determined one or more products on the health application. The server system is caused to receive a user input indicating selection of two or more products and compare the two or more products including the at least one nutrient. At least quantities of each ingredient comprised in the two or more products are compared. Further, the server system is caused to determine at least one product from the two or more products for providing recommendation to the user based on the user profile and the comparison of the two or more products. The server system is further caused to facilitate, on the health application, display of the comparison of at least a quantity of each ingredient included in the two or more products and the recommendation of the at least one product from the two or more products for the user.

Other aspects and example embodiments are provided in the drawings and the detailed description that follows.

BRIEF DESCRIPTION OF THE FIGURES

For a more complete understanding of example embodiments of the present technology, reference is now made to the following descriptions taken in connection with the accompanying drawings in which.

Figure 1:
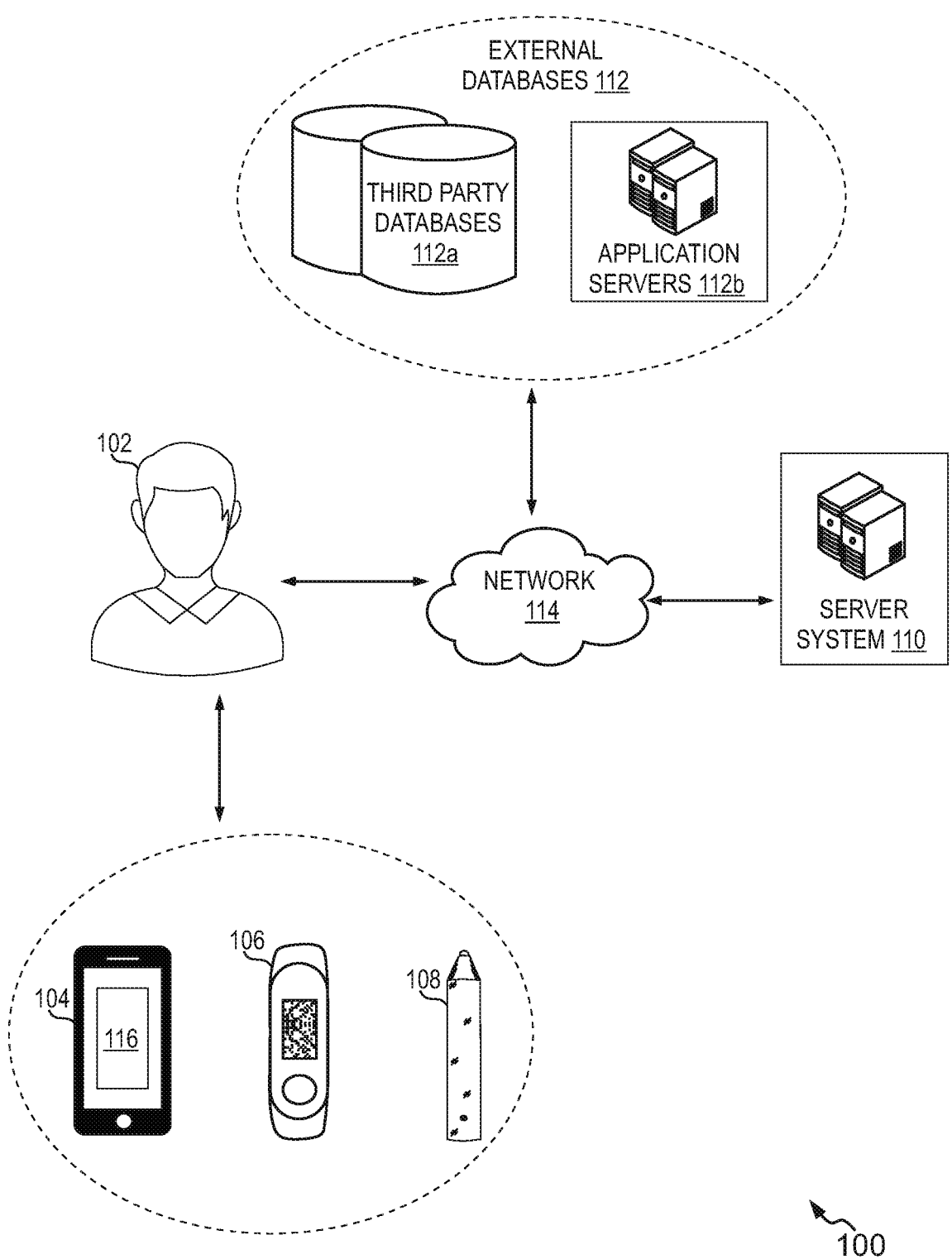
FIG. 1 illustrates an example representation of an environment, in which at least some embodiments of the present disclosure can be implemented.

The drawings referred to in this description are not to be understood as being drawn to scale except if specifically noted, and such drawings are only exemplary in nature.

DETAILED DESCRIPTION

In the following description, for purposes of explanation, numerous specific details are set forth in order to provide a thorough understanding of the present disclosure. It will be apparent, however, to one skilled in the art that the present disclosure can be practiced without these specific details.

Reference in this specification to "one embodiment" or "an embodiment" means that a particular feature, structure, or characteristic described in connection with the embodiment is included in at least one embodiment of the present disclosure. The appearances of the phrase "in an embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

Moreover, although the following description contains many specifics for the purposes of illustration, anyone skilled in the art will appreciate that many variations and/or alterations to said details are within the scope of the present disclosure. Similarly, although many of the features of the present disclosure are described in terms of each other, or in conjunction with each other, one skilled in the art will appreciate that many of these features can be provided independently of other features. Accordingly, this description of the present disclosure is set forth without any loss of generality to, and without imposing limitations upon, the present disclosure.

Overview

Various example embodiments of the present disclosure provide systems and methods for managing nutrient intake of a user associated with a user device.

The present disclosure describes a server system that enables management of nutrient intake of the user through a health application installed in the user device. The server system is configured to manage the health application installed in the user device for managing the nutrient intake. As such, the user provides a request to the server system through the health application for registering the user with the server system. The request may include information pertaining to the user such as name, age, height, weight, calorie intake, and the like. Upon receiving the request, the server system accesses and retrieves user information from one or more sources such as external databases, wearable devices, and nutrient trackers. The server system creates a profile of the user (hereinafter referred to as "user profile") in the health application based on the user information.

Further, the server system determines at least one nutrient based on processing various user information and recommends the nutrients to the user. The server system is configured to determine one or more products from a plurality of products based on the determination of the nutrients. The server system creates a nutrition diary including the one or more products that are owned by the user. Further, the server system determines at least one nutrition goal and a nutrition plan based on the user information. The nutrition plan includes the dosage values of the one or more products and time and a combination of intake of dosage value of a particular product. As such, the user needs to consume the nutrients from the one or more products so as to complete the nutrient goal. Further, the user may indicate consumption of a dosage of at least one of the one or more products in the nutrition diary on the health application. Furthermore, the user provides a plurality of signals indicating consumption of dosage of one or more products at predetermined time intervals to the server system through the health application. As a result, the server system updates a quantity of each product in a digital inventory of the health application on the consumption of dosage of the one or more products.

In addition, the server system calculates energy levels based on the nutrient intake by consuming the one or more products. The server system also determines the source of each nutrient consumed by the user. The source of each nutrient corresponds to the one or more products owned by the user in the nutrition diary. Further, the server system is configured to create a nutrition log by plotting the dosage of nutrient intake and the time of nutrient intake. In one case, the server system provides a notification to the user on the health application reminding about nutrient intake of a particular product in the nutrition diary to complete the nutrient goal.

Additionally, the server system sends a reminder to the user through the health application when the quantity/servings of the one or more products in the digital inventory is less than a predetermined threshold value. The reminder indicates the user to refill the at least one product. Further, the server system is configured to compare two or more products including the at least one nutrient. As such, the user provides input in the health application related to the selection of the two or more products from the one or more products displayed in the health application. The server system determines at least one product from the two or more products for recommendation to the user based on the user profile and the comparison of the two or more products. More specifically, the server system compares the two or more products on an ingredient level to recommend the at least one product to the user.

The server system rewards the user with reward points holding monetary value based on the completion of at least one nutrient goal. The reward points may be rewarded based on completion of the nutrient goal on a daily, weekly, monthly basis. Further, the reward points are utilized by the user for purchasing one or more products from the plurality of products offered by the health application. As such, the reward points for purchasing one or more products are determined by the server system.

The server system further creates a user code that maps the user to the user profile. The unique identification code is generated by appending the user information such as the list of products, the nutrition log, the digital inventory, and the reward points associated with the user. The user code is shared by the user to other users (e.g., registered users and unregistered users) by the health application via one or more messaging channels. The unique identification shows engagement of the user with the health application to the other users. In other words, the unique identification code enables an interactive platform in the health application. In an embodiment, the server system may receive a request from the user to provide one or more products including one or more nutrients or a combination of nutrients based on user requirements. The user requirements may be for including certain nutrients, preference of ingredients as per user's choice or health conditions. For example, a user may want a vegetarian product. In response, the server system may identify one or more vendors capable of manufacturing the required one or more products. The server system may share user profile and the user requirements with the vendor to manufacture one or more products that are customized according to user's preferences.

Various example embodiments of present invention are described hereinafter with reference to FIGS. 1 to 12.

FIG. 1 illustrates an exemplary representation of an environment 100, in which at least some example embodiments of the present disclosure can be implemented. Although the environment 100 is presented in one arrangement, other embodiments may include the parts of the environment 100 (or other parts) arranged otherwise depending on, for example, monitoring nutrition intake of an individual through a nutrition management application (hereinafter referred to as "health application"). The environment 100 includes a user 102 associated with a user device 104 (exemplary depicted to be a "mobile phone"), a wearable device 106, and a nutrient tracker 108. In one example, the wearable device 106 may be a wearable fitness band that tracks sleeping hours, number of steps, number of calories burnt, heart rate and the like. The nutrient tracker 108 may count calorie intake, track diet, and other health metrics. Further, the environment 100 includes a server system 110 and external databases 112. The external databases 112 include one or more third party databases 112a and one or more application servers 112b associated with one or more applications used by the user 102.

The wearable device 106 and the nutrient tracker 108 may be connected with the user device 104 via a short range communication protocols such as, but not limited to, Bluetooth, ZigBee, Z-wave and the like. The wearable device 106 may be configured to track various parameters associated with the user 102 such as, but not limited to, sleep activity, exercise time, calorie burnt, pulse rate and the like. Further, the nutrient tracker 108 may be configured to track one or more nutrients consumed by the user 102, supplement consumption activities and the like. The nutrient tracker 108 is configured to determine content of each nutrient in user's body over a period of time. The one or more third party databases 112a may include information associated with the user 102 related to body/blood tests, health activities, medical consultation details, type of products consumed and the like. In one embodiment, the one or more applications used by the user 102 may be installed in the user device 104. The one or more applications may include applications associated with the wearable device 106 and the nutrient tracker 108. Examples of the one or more applications may be a meditation application, a fitness application, a nutrient tracker application, a sleep monitoring application, a health center application and the like. In general, the information pertaining to the user 102 stored in the external databases 112, and the one or more parameters determined by the wearable device 106 and the nutrient tracker 108 constitute user information. The user information is utilized by a health application 116 installed in the user device 104 and communicably coupled with the server system 110 for monitoring the nutrient intake of the user 102. This will be explained in detail in further paragraphs.

The server system 110, the external databases 112, the user 102 associated with the user device 104, the wearable device 106, and the nutrient tracker 108 are communicably coupled with each other via a network 114. Various entities in the environment 100 may connect to the network 114 in accordance with various wired and wireless communication protocols, such as, Transmission Control Protocol and Internet Protocol (TCP/IP), User Datagram Protocol (UDP), $2^{nd}$ Generation (2G), $3^{rd}$ Generation (3G), $4^{th}$ Generation (4G), $5^{th}$ Generation (5G) communication protocols, Long Term Evolution (LTE) communication protocols, or any combination thereof. The network 114 may include, without limitation, a local area network (LAN), a wide area network (WAN) (e.g., the Internet), a mobile network, a virtual network, and/or another suitable public and/or private network capable of supporting communication among two or more entities illustrated in FIG. 1, or any combination thereof.

The environment 100 including the server system 110 is configured to perform one or more of the operations described herein. In general, the server system 110 is configured to monitor and/or manage the nutrient intake of the user 102 through the health application 116 installed in the user device 104. Further, the components and/or features associated with the health application 116 may rest in the server system 110 and the user device 104. The server system 110 may provide an instance of the health application 116 upon receiving a request for downloading the health application 116 from the user device 104. In one embodiment, the health application 116 may be downloaded from application stores such as, but not limited to, Google Play store, Application store, or from any other online website. In another embodiment, the health application 116 may be factory installed in the user device 104 and managed by the server system 110.

The health application 116 may access the external databases 112 via the network 114 for managing the nutrient intake of the user 102. More specifically, upon receiving a user request for registration, the server system 110 is configured to create a user profile of the user 102 in the health application 116 based on the user information. The user information is retrieved from at least one of the external databases 112, the wearable device 106, the nutrient tracker 108, and a user input manually entered by the user. Additionally, the health application 116 periodically receives the user information from at least the external databases 112, the wearable device 106 and the nutrient tracker 108 to update the user profile of the user 102.

The server system 110 managing the health application 116 determines at least one nutrient based on the user information or the user profile of the user 102. Further, the server system 110 may recommend one or more products, dosage values, serving amounts based on the user information. The server system 110 may compare two or more products and display the comparison to the user 102 on the health application 116. Upon comparison of the two or more products, the server system 110 recommends a suitable product to the user 102 which suits to the user profile. Further, the user 102 may purchase the one or more products offered by the health application 116 to consume nutrients.

In an embodiment, the server system 110 is configured to determine at least a nutrient goal and a nutrition plan for the user 102 based on the user information. The nutrition plan includes identifying one or more products and the dosage values of the one or more products. Further, the nutrition plan may specify the time and combination of intake of dosage value of a particular product. For instance, the nutrition plan may be determined on a daily basis which indicates the nutrients and servings to be consumed daily to complete the nutrient goal. The server system 110 may revise the nutrition plan and the nutrient goal after predetermined time duration. The revision in the nutrition plan and the nutrient goal may be based on periodically receiving the user information pertaining to the user 102 from user input in the health application 116, the external databases 112, the wearable device 106, and the nutrient tracker 108.

The user 102 may consume the nutrients according to the nutrition plan by selecting corresponding product, dosage and servings pertaining to each nutrient. The user 102 may manually input the intake of consumption of a serving of at least one product by a logging mechanism which will be explained in detail in further paragraphs. Upon achieving the nutrition goal by consuming appropriate nutrients as determined in the nutrition plan by the user 102, the user 102 is rewarded with reward points. The reward points hold monetary value which may be used and/or redeemed to purchase products offered by the health application 116.

Further, the server system 110 is configured to provide a user code (also referred to as a unique identification code) to a user 102. The user 102 may share the user code with user's friends. Using the user code of the user 102, the user's friends may view the profile of the user 102. Furthermore, each product may be associated with a product code that may be used to access the product information like ingredients, nutrient percentage, manufacturer, manufacture date, expiry date etc. It is noted that a user code is unique for each user and a product code is unique for each product.

Figure 2:
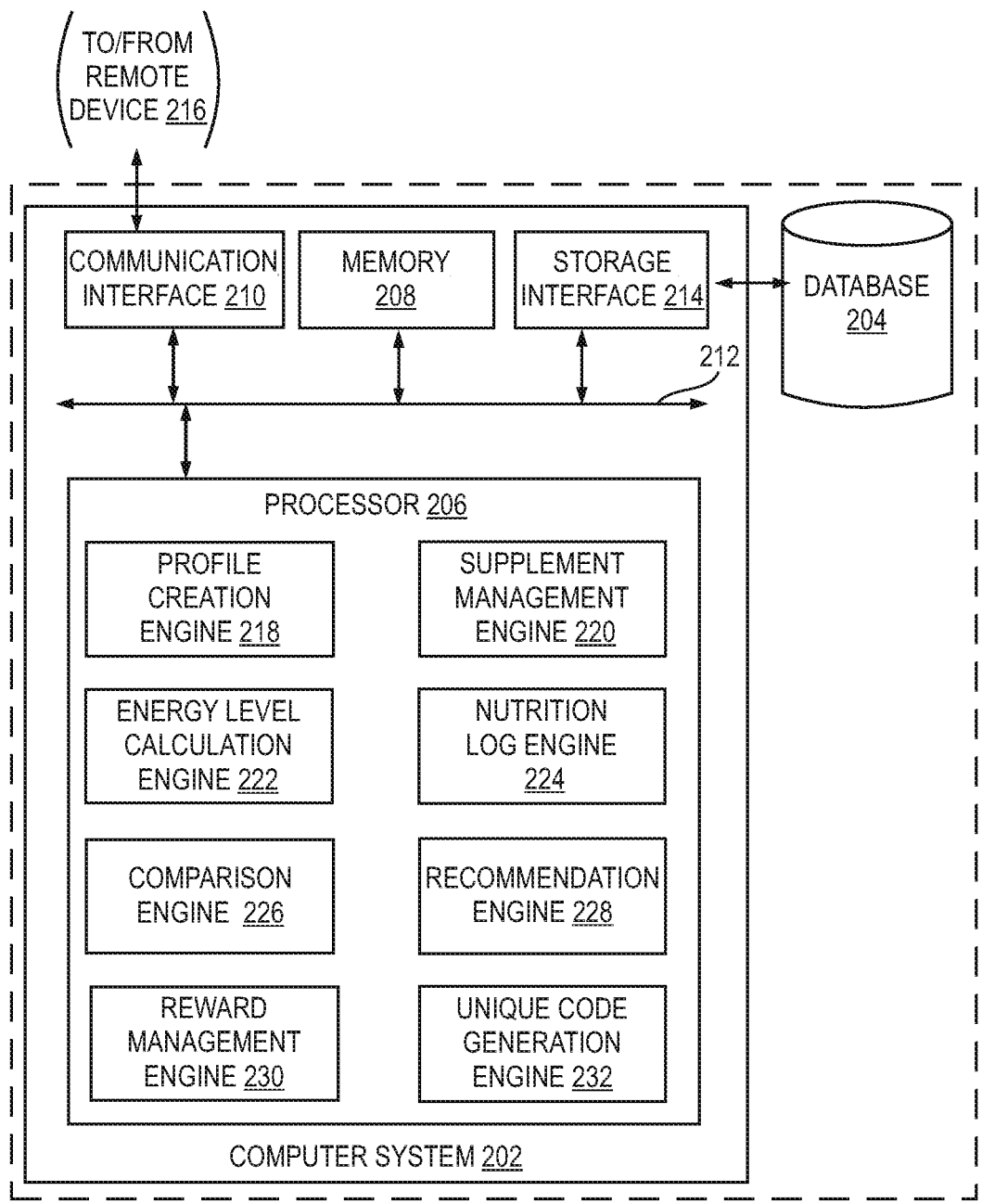
FIG. 2 illustrates a simplified block diagram of a server system used for managing nutrient intake of a user via a health application on a user device, in accordance with an embodiment of the present disclosure.

FIG. 2 illustrates a simplified block diagram of a server system 200 used for managing nutrient intake of the user 102 via the health application 116 on the user device 104, in accordance with one embodiment of the present disclosure. Examples of the server system 200 include, but are not limited to, the server system 110 as shown in FIG. 1. The server system 200 includes a computer system 202 and a database 204. The computer system 202 includes at least one processor 206 for executing instructions, a memory 208, a communication interface 210, and a storage interface 214. The one or more components of the computer system 202 communicate with each other via a bus 212.

In one embodiment, the database 204 is integrated within the computer system 202 and configured to store an instance of the health application 116 and one or more components of the health application 116. The one or more components of the health application 116 may be, but not limited to, information related to a plurality of products, nutrient percentage of each product, source of nutrients in each product, user profiles associated with a plurality of users and the like. The computer system 202 may include one or more hard disk drives as the database 204. The storage interface 214 is any component capable of providing the processor 206 an access to the database 204. The storage interface 214 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing the processor 206 with access to the database 204.

The processor 206 includes suitable logic, circuitry, and/or interfaces to execute computer readable instructions for managing nutrient intake of the user 102 through the health application 116 installed on the user device 104. Examples of the processor 206 include, but are not limited to, an application-specific integrated circuit (ASIC) processor, a reduced instruction set computing (RISC) processor, a complex instruction set computing (CISC) processor, a field-programmable gate array (FPGA), and the like. The memory 208 includes suitable logic, circuitry, and/or interfaces to store a set of computer readable instructions for performing operations. Examples of the memory 208 include a random-access memory (RAM), a read-only memory (ROM), a removable storage drive, a hard disk drive (HDD), and the like. It will be apparent to a person skilled in the art that the scope of the disclosure is not limited to realizing the memory 208 in the server system 200, as described herein. In some embodiments, the memory 208 may be realized in the form of a database server or a cloud storage working in conjunction with the server system 200, without deviating from the scope of the present disclosure.

The processor 206 is operatively coupled to the communication interface 210 such that the processor 206 is capable of communicating with a remote device 216 such as, the user device 104, the external databases 112, the wearable device 106, and the nutrient tracker 108 or with any entity connected to the network 114 as shown in FIG. 1.

It is noted that the server system 200 as illustrated and hereinafter described is merely illustrative of an apparatus that could benefit from embodiments of the present disclosure and, therefore, should not be taken to limit the scope of the present disclosure. It is noted that the server system 200 may include fewer or more components than those depicted in FIG. 2.

In one embodiment, the processor 206 includes a profile creation engine 218, a supplement management engine 220, an energy level calculation engine 222, a nutrition log engine 224, a comparison engine 226, a recommendation engine 228, a reward management engine 230 and a unique code generation engine 232. As such, the one or more components of the processor 206 as described above are communicably coupled with the health application 116 of the user device 104 and manage the nutrients intake of the user 102.

The profile creation engine 218 includes a suitable logic and/or interfaces for creating a user profile in the health application 116. The profile creation engine 218 creates the user profile based on the user information extracted from the database 204 or external databases 112. The profile creation engine 218 creates a micronutrients profile (i.e., the user profile) corresponding to each user (e.g., the user 102) based on vitamins, minerals, phytonutrients, herbs, nootropics, nutricosmetics, and other dietary type supplements. The profile creation engine 218 receives a request to register a user from a health application 116 installed in a user device 104. In one embodiment, the request may include information pertaining to the user 102, such as, but not limited to, name, age, height, weight, calorie intake, health condition, and the like. The profile creation engine 218 may further access the user information from the third party databases 112a, the one or more application servers 112b, the one or more parameters determined by the wearable device 106 and the nutrient tracker 108 for creating the user profile. As such, the user profile includes information related to nutrient consumption, dosage values, energy level based on amount of consumption of the nutrients, consumption activity, one or more products possessed by the user, at least one nutrient goal, and a nutrition plan. The profile creation engine 218 is configured to customize the user profile based on periodically receiving the user information and user interactions with the health application 116 over a period of time.

Upon creation of the user profile, the user 102 is recommended one or more products including at least one nutrient to be consumed to maintain the dietary requirements of the user 102 in a sustainable manner. The supplement management engine 220 is configured to determine the at least one nutrient for the user 102 based on the user profile. The supplement management engine 220 further determines the one or more products from a plurality of products that include the at least one nutrient. The one or more products determined by the supplement management engine 220 of the server system 200 are displayed on the health application 116 installed on the user device 104. Further, based on the user profile, the supplement management engine 220 also determines the dosage values, serving amounts, the time of consumption of the one or more products, and the manner in which the one or more products must be consumed. In one embodiment, the user 102 may provide information related to the products owned by the user 102 in the health application 116. In this case, the supplement management engine 220 may update the user profile with the information provided by the user 102 related to the products and the dosage values. Further, the list of one or more products owned by the user 102 and corresponding dosage values and serving amounts are displayed on the health application 116. In other words, the list of products, the dosage values and the servings displayed in the health application 116 are collectively referred to as nutrition diary which will be explained with reference to FIG. 3. The dosage values, the list of products, the manner in which the products are to be consumed, the time of consumption, and the servings of each product are collectively referred to as the nutrition plan of the user 102.

The supplement management engine 220 is configured to determine at least one nutrient goal associated with the user 102 based on the user profile. For instance, if the nutrient goal is set on a daily basis, to complete daily nutrient goal, the user 102 should intake each nutrient of determined dosages and servings in the nutrition plan. In an embodiment, each nutrient and the goals for each nutrient may be represented in a graphical representation (e.g., spider web/ radar chart) by the nutrition log engine 224 (see, FIG. 5A). In another embodiment, the nutrition log engine 224 may represent each nutrient and daily consumption in a data representation form indicating data of the intake of each nutrient in percentages (see, FIG. 5B).

In one scenario, the user 102 may be recommended products with similar nutrients. The user may wish to compare various aspects of the products to select a suitable product. In an embodiment, the comparison engine 226 receives user selection of two or more products in the health application 116. As such, the comparison engine 226 is configured to compare the two or more products on an ingredients level or nutrient level. In one embodiment, the user 102 may scan barcode corresponding to each product and/or capture a product label of each product for comparison. Upon comparison, the comparison engine 226 is configured to facilitate a display of the selected products and a comparison chart on the health application 116 on the user device 104 (see, FIG. 10). For instance, a comparison of the two or more products may be indicated in a tabular form depicting percentage of nutrients, energy levels associated with each nutrient of the product, source of each nutrient in the product, the nutrient goal of each nutrient, and the like (see, FIG. 10).

Further, the recommendation engine 228 communicably coupled to the comparison engine 226 is configured to recommend a suitable product to the user 102 based on the comparison chart and the user profile of the user 102. The recommended product and the dosage value may be updated in the user profile by the supplement management engine 220 for managing nutrient intake of the user 102. Additionally, the recommendation engine 228 may recommend certain products based on the user's consumption habits, used supplements, user preferences and the like.

In an embodiment, the comparison engine 226 and the recommendation engine 228 may operate collectively to recommend a suitable product to the user 102 based on the user profile while purchasing the products from online websites or the health application 116. For instance, at the time of purchase, the user 102 may view comparison of two products which includes Omega-3 nutrient containing different percentages of Omega-3 per serving or different sources of Omega-3. In this case, the comparison engine 226 compares both the products on an ingredient level and lists out the total energy levels or calories corresponding to both the products and the energy level or percentage of Omega-3 per serving. The recommendation engine 228 may recommend, to the user, that product out of the two products which requires less servings to be taken by the user to achieve the nutrient goal of the nutrient Omega-3. In an embodiment, the recommendation engine 228 may recommend the product based on consumption habits of the user 102 which includes the type of serving (e.g., soft gel or capsule), size of serving and the like. In another embodiment, the comparison engine 226 and the recommendation engine 228 may recommend one of the two similar products by taking into consideration multiple nutrients included in the products to achieve multiple nutrients goal determined in the user profile.

Additionally, the recommendation engine 228 is configured to recommend products and/or dosage to the user 102 based on upcoming activities listed in the user profile, such as sports competition, extended hours under the sun, travel and the like. As such, the products recommended for the above-mentioned activities may result in boosting up of energy levels or providing sufficient nutrient intake to the user 102 for achieving the fitness level for the activities. Further, operation of the comparison engine 226 and the recommendation engine 228 improves based on periodically updating the user profile with user information from the one or more sources such as, the external databases 112, the wearable device 106, and the nutrient tracker 108.

The listing of parameters such as the one or more products, nutrients associated with each product, quantity of the products remaining, and the servings of each product based on the nutrition plan and the nutrition goal is displayed on the health application 116. Further, the above-mentioned parameters are collectively referred to as a digital inventory (see, FIG. 6). As such, the supplement management engine 220 is configured to monitor the digital inventory associated to the user 102 based on consumption of servings of the one or more products by the user 102. Particularly, the user 102 may provide a first signal to the server system 200 through the health application 116 indicating consumption of the one or more products. The first signal may be, but not limited to, a tactile input, a voice input, a gesture input and the like. Further, based on the consumption, the supplement management engine 220 calculates the amount of servings to be consumed to complete the nutrient goal and servings of the products remaining for each product possessed by the user. The supplement management engine 220 updates the digital inventory of the user 102 based on the calculation. The supplement management engine 220 provides information related to the source of each nutrient consumed by the user 102 on the health application 116. As such, the source of each nutrient corresponds to at least one of the one or more products.

In addition, the supplement management engine 220 may notify the user 102, if a product in the digital inventory is likely to go out of stock or is less than a pre-determined threshold. In other words, the supplement management engine 220 of the server system 200 is configured to send a second signal on the health application 116. The second signal is indicative of a reminder to refill the at least one product. In one scenario, upon receiving the notification, the user 102 may order the at least one product. Accordingly, the supplement management engine 220 may update the digital inventory corresponding to the user. In another scenario, the supplement management engine 220 may order the products automatically based at least on the user information in the user profile, availability of products in store, quantity of products remaining in the digital inventory, delivery time of the products and the like. Thus, monitoring the products in the digital inventory ensures that the user 102 intakes the nutrient without interruption. Further, the supplement management engine 220 is configured to track contents of each supplement and to record feedback on the products based on the user consumption of the products. For example, if 30 tablets are listed on the product label, however when the user 102 consumed the product, only 29 tablets were found. In that case, a defect in manufacturing is recorded and thus feedback on the product is recorded.

In one embodiment, the user 102 may request the server system 200 to add a product not listed in the plurality of products, to the user profile. In this scenario, the supplement management engine 220 triggers an image capturing module of the user device 104 either to scan the product code or capture the product label. In an example, the product code may be a barcode or a 2-D Quick Response (QR) code. The supplement management engine 220 retrieves the information of the product encoded in the product code or detects the contents in the product label. Further, based on the information retrieved, the supplement management engine 220 adds the product, along with the number of servings in each product, to the list of products owned by the user 102 in the digital inventory. Furthermore, the product added in the user profile may be stored in the database 204 and augment the plurality of products in the database 204.

In another embodiment, the user 102 may manually add the non-listed products by entering the information in the health application 116. The information may be, but is not limited to, product name, serving type, nutrients type, total serving amounts, expiry date and the like.

In an embodiment, if a product that the user 102 possesses and wishes to add to the digital inventory is not registered with the server system 200, the user 102 may include the product by either scanning the product code or capturing the image of the product label. In another embodiment, the user 102 may utilize the image capturing module of the user device 104 to scan the product code for purchasing the products. In yet another embodiment, the comparison engine 226 may trigger the image capturing module of the user device 104 to capture the product code or the product label of the two or more products for providing comparison of the two or more products to the user 102.

Further, the servings or dosage values of each nutrient consumed by the user 102 is recorded in a nutrition log by the nutrition log engine 224. In particular, the nutrition log engine 224 records the time of intake of nutrient and the servings of the products listed in the user profile. For example, the nutrition log engine 224 may create a statistical representation (e.g., bar graph) indicating each nutrient, the time of nutrient intake (e.g., on a daily basis) etc. As such, the nutrition log enables the user 102 to manage the nutrient intake, and to keep a check on the nutrient goal. In an embodiment, the nutrition log may be customized by the nutrition log engine 224 based on a user selection of the nutrients in the health application 116. For example, the user 102 may select only two nutrients to be represented on the nutrition log by the nutrition log engine 224. In this scenario, the user 102 may compare and manage the nutrient intake of the two nutrients based on the information from the nutrition log.

In one scenario, the user 102 may consume one nutrient as opposed to the other nutrient in a single day or over a period of time. In another scenario, the user 102 may like to consume certain nutrients in a proportional manner. As such, the nutrition log engine 224 may create a set of reminders for each nutrient to notify the user 102. For example, for a user, if the nutrient goal for Vitamin C and Vitamin D is that one serving of product corresponding to each of the two nutrients is to be taken on a daily basis and if the user has consumed only a product containing Vitamin C and not Vitamin D then the nutrition log engine 224 provides a notification to the user to consume the product containing Vitamin D on the health application 116.

Additionally, the nutrition log engine 224 may set reminders to consume certain products and/or to achieve the nutrient goal based on user consumption activity. The reminders to consume the products and/or achieve the nutrient goal may be customizable by the user 102 either at a product level or the nutrients level. For instance, the nutrition log engine 224 may provide a reminder/notification to consume certain products at pre-determined times to complete the nutrient goal for the user 102 or based on the consumption activity. In one embodiment, the nutrition log engine 224 may also provide notification to the user 102 through the health application 116 to consume one or more products based on location (e.g., gym, office, home) of the user 102.

Further, the nutrition log engine 224 may be configured to provide a search feature in the health application 116. The user 102 may search for the nutrients by entering forms of chemicals in the health application 116. For example, Vitamin K includes more than one form, K1 (phylloquinone) & K2 (menaquinone). Further, Vitamin K2 may include two forms menaquinone-4 (MK-4) & menaquinone-7 (MK-7)). In this case, the user 102 may enter the chemical form of the nutrients (e.g., K1 or K2 for vitamin) which allows searching of ingredients at micronutrients level.

The energy level calculation engine 222 is configured to calculate the energy level of the user 102 based on the nutrient intake of the user 102. In one example, the energy level may be a number ranging from 0-100 or 0-1000 or as percentage or any other type of data representation which will be explained in further paragraphs. In addition, the calculation of the energy level is based on various metrics such as, but not limited to, the serving amounts, type/quality of nutrients consumed, completion of a nutrient goal and a nutrition plan, and the like. In one embodiment, the supplement management engine 220 may provide recommendation to consume particular products to achieve particular energy levels or to complete the nutrient goals (e.g., daily).

Further, the user 102 is rewarded with reward points based on completion of the nutrient goal by consuming the servings of one or more products as determined in the nutrition plan. More specifically, the reward management engine 230 is configured to reward the user 102 with reward points based on completion of the nutrient goal of each nutrient. The reward points are depicted in the user profile on the health application 116 (see, FIG. 3A). The reward points hold monetary value. In an embodiment, the reward points may be awarded to the user 102 based on completion of daily nutrient intake (i.e., daily nutrient goal). In another embodiment, the reward points may be awarded based on completing the daily nutrient goal consecutively over a period of time (e.g., weekly, monthly and the like). For example, if the user completes a streak of nutrient intake for 3 days in a row, the user is rewarded with reward points on the third day along with reward points for completing the daily nutrient goal. In some embodiments, the reward points may also be rewarded to the user 102 for activities, such as attending sports events, workshops and the like.

In an embodiment, the monetary value associated with each reward point may vary based on membership type (e.g., gold, premium, platinum etc.) subscribed by the user 102 at the time of registration with the server system 200. Further, the reward points holding the monetary value are referred to as digital currency. Thus, the reward points are utilized for purchasing one or more products from a store or a digital store associated with the server system 200. In one form, the comparison engine 226 and the recommendation engine 228 collectively operate to redeem the reward points for each product based on the comparison chart to avail discounts on purchasing the products (see, FIG. 10).

Further, the information in the user profile related to the list of products, the nutrition log, the digital inventory, and the reward points may be shared to other registered users of the health application 116 via a user code of the user 102. The user code is generated and managed by the unique code generation engine 232 based on the information in the user profile as described above. In general, the user code maps the user 102 to the user profile. Further, the content appended to the user code associated with the user profile may be updated periodically. Further examples of the user code include, but are not limited to, a barcode or a 2-D Quick Response (QR) code. Each user has a unique user code.

The user code may be shared by the user 102 to other registered users by the health application 116 via one or more messaging channels. The user code allows the user 102 to connect with other registered users in the health application 116. As such, the user code allows the user 102 to at least communicate and to share the user profile to the registered users of the health application 116. In other words, the health application 116 may be used as an interactive platform by utilizing the user code.

In one embodiment, the server system 200 may notify the user 102 about the nearby registered users in the health application 116 based on GPS (i.e., global positioning services) data from the user device 104. In this scenario, the user 102 may connect with the nearby registered users by sharing the user code. For example, the server system 200 may notify the user 102 if another user is nearby by providing information such as, the profile name, distance from the user 102 and the like. The information to be displayed to the nearby users may be customized by the privacy setting of each user.

Additionally, the user 102 may create groups of the connected users in the interactive platform of the health application 116 for managing the nutrient intake of the user 102 or the other users. For example, a mother may add profiles of her kids, which allows the server system 200 to remind the mother about the nutrient intake of her kids. Further, the server system 200 may allow the mother to interact and remind to intake of nutrients or supplements to the kids. In one embodiment, the unique code generation engine 232 may be configured to create a group identification code (group ID). The group ID represents the users in the group and exhibits same functionality to that of the single user code associated with a user profile.

In one embodiment, the user code may be shared with users who are not registered with the server system 200. In one embodiment, the server system 200 directs the unregistered user to the application store to download the health application 116 upon clicking on the user code. In another embodiment, the server system 200 may provide an unregistered user with an instance of the health application 116 on a user device associated with the unregistered user. Thus, the user code also acts as a marketing tool to increase number of users using the health application 116. In an embodiment, the user 102 may utilize the user code to share the reward points with the registered users, the unregistered users or with the merchants for purchase of products.

The unique code generation engine 232 may generate product codes corresponding to each of the products registered with the server system 200. In an embodiment, if a user possesses a new product which is not registered with the server system 200, the user may send, to the server system 200, a scanned image of the new product or provide a product label of the new product. The unique code generation engine 232 may be configured to generate a product code for the new product based on information associated with the scanned product or provided by the product label. More specifically, the supplement management engine 220 determines the ingredients on the product label of the product. Thereafter, the unique code generation engine 232 generates the product code of the product. Further, the product with the product code is added to the list of products in the user profile and to the plurality of products in the database 204 for future use of the user 102.

The one or more components of the server system 200 may receive the user inputs on the health application to perform the one or more operations as described above. The user 102 may provide inputs in corresponding user interfaces rendered on the user device 104 by the health application 116. The user interfaces rendered by the health application 116 for receiving the user inputs are herein described in detail in further paragraphs.

Figure 3A:
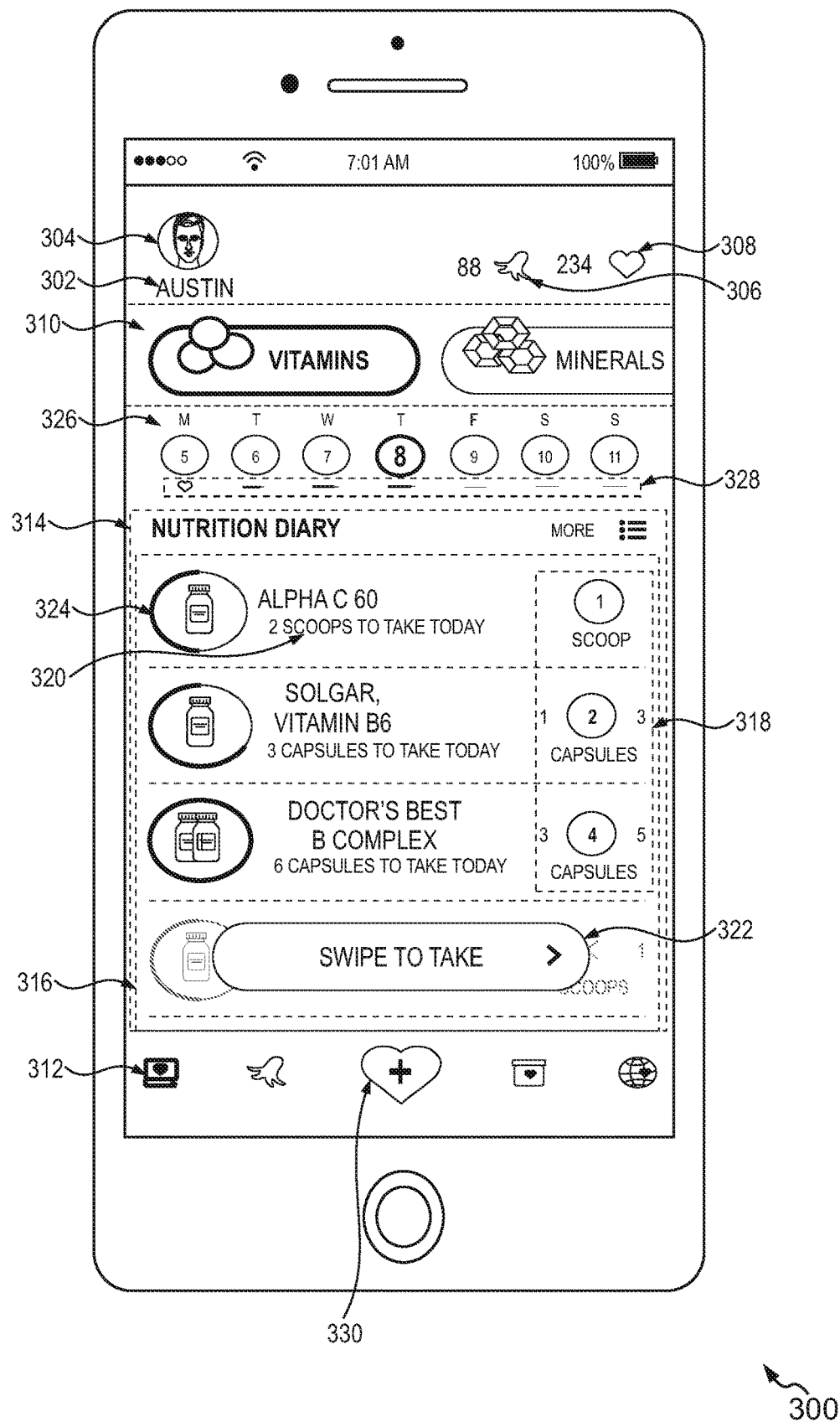
FIG. 3A illustrates an exemplary representation of a user interface (UI) displaying a list of products in user profile to the user, in accordance with an embodiment of the present disclosure.

Referring now to FIG. 3A, which illustrates an exemplary representation of a user interface (UI) 300 displayed to a user, such as the user 102, on a health application, such as the health application 116. The UI 300 depicts a list of products owned by the user. The UI 300 renders multiple information fields such as a username 302 (exemplary shown as 'Austin'), a profile photo 304 of the user, an energy level indicator 306 (exemplary depicted to be '88'), and a reward points indicator 308 (exemplary depicted as 'heart icon' and associated with a value '234'). Further, the UI 300 depicts a nutrient section 310 which includes each nutrient categorized individually (exemplary depicted to be 'vitamins' and 'minerals'). The categorization of each nutrient as vitamins and minerals may be performed by the supplement management engine 220 as explained with reference to FIG. 2. For illustrative purpose, vitamins are selected (exemplary highlighted by bold indicating the selection of the vitamins) in the nutrient section 310. Further, the selection of vitamins should not be taken to limit the scope of the present disclosure.

The UI 300 depicts a nutrition diary 314 based on user selection of an actionable icon 312. The nutrition diary 314 includes a list of products 316 (hereinafter interchangeably referred to as 'the products 316') owned by the user 102, serving amounts 318 and dosage values 320 associated with each product. The serving amounts 318 may be, but not limited to, scoops, capsules based on the type of product (i.e., the products 316) owned by the user 102 in the nutrition diary 314. The dosage value 320 provides information of the dosage to be consumed for the product from the list of products 316. For example, the UI 300 depicted to include the product (exemplary depicted to be 'Alpha C 60') from the list of products 316 is associated with servings amount depicted to be '1 scoop' and the dosage value to be consumed (depicted to be '2 scoops to take today'). The UI 300 further includes an actionable button 322 associated with the text 'SWIPE TO TAKE'. The user may swipe the actionable button 322 to record a consumption of the products 316 listed in the nutrition diary 314. As such, the input for consuming the products 316 is referred to as the first signal as described with reference to FIG. 2. In one scenario, the user 102 swipes on a single product from the list of products 316 to consume the product upon selection of the serving amounts 318 associated with the product. In another scenario, the user 102 may select the serving amounts 318 of multiple products from the list of products 316 and swipe on each of the product to consume at the same time.

Further, each product from the list of products 316 includes a status bar 324 (exemplary depicted as 'circle' around the product icon). The status bar 324 around the product icon of each product indicates the amount of dosage values consumed by the user 102. In one case, if the user 102 has not consumed the dosage value associated with the product, the status bar 324 is depicted to be full circle around the product icon. In another case, if the user 102 has consumed half the dosage value of the product, the status bar 324 around the product icon will be half full (dosage to be consumed is represented in bold in the status bar 324). Further, if the user 102 consumes all the dosage values of the product, the status bar 324 will be zero full.

The UI 300 further includes a calendar section 326 depicting days (exemplary depicted by 'first alphabet' of the day) and a date. For example, the alphabet of the day is depicted as 'T' which indicates Thursday and the date associated with the day is depicted to be '8' in the calendar section 326. The selection of the date and day in the calendar section 326 is exemplary depicted to be a 'circle' around the date. Further, the calendar section 326 depicts the nutrient goal bar 328 below each date and day depicted in the UI 300. The nutrient goal bar 328 provides information on status of the nutrient goal on each day listed in the calendar section 326 to the user 102. In one scenario, if the nutrient goal is completed on a particular day (exemplary depicted to be 'Monday'), the nutrient goal bar 328 may be replaced with the heart icon.

Figure 3B:
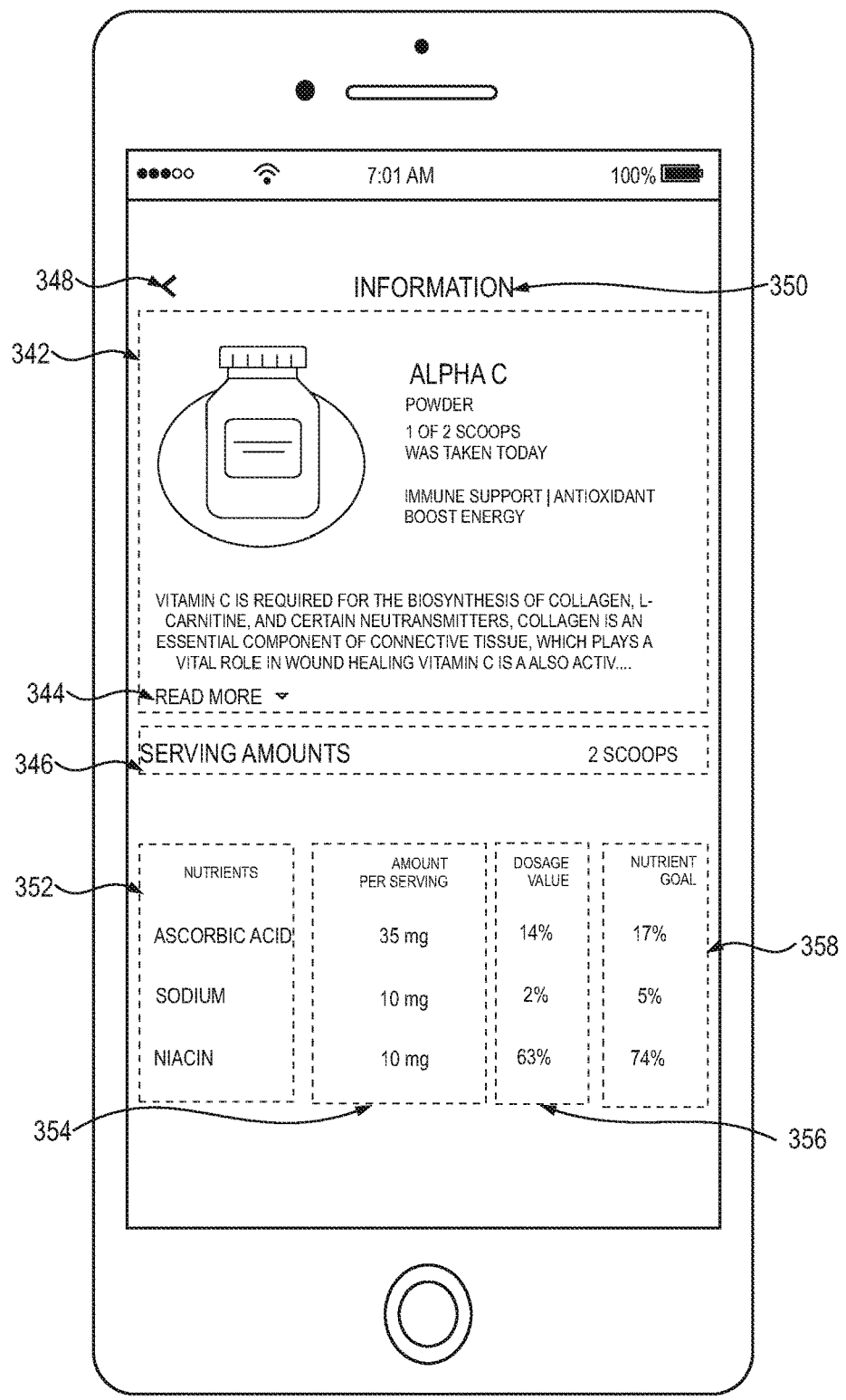
FIG. 3B illustrates an exemplary representation of a UI displaying product information of a product to the user, in accordance with an embodiment of the present disclosure.

Further, the user 102 may provide a selection input on a product from the list of products 316 depicted in the UI 300. In this scenario, as show in FIG. 3B, the user 102 may be prompted with a UI 340 that depicts the product information based on the user selection of the product from the list of products 316. The UI 340 is depicted to include a title 350 associated with the text 'INFORMATION' and a product information section 342 including product information, such as, the product name, product photo, type of product, detailed information about the product, and the dosage values (e.g., as shown in FIG. 3B). The dosage values in the product information section 342 correspond to information related to intake of the dosage value of the product (exemplary depicted to be '1 of 2 scoops was taken today'). The UI 340 is depicted to include a drop down menu 344 associated with the text 'Read more' to display the remaining portion of the detailed information of the product (as shown in FIG. 3B). The UI 340 is depicted to include serving amounts 346 (exemplary depicted to be '2 scoops'). Additionally, the UI 340 is depicted to include four columns 352, 354, 356 and 358 that include list of nutrients present in the product, amount per servings, dosage values offered by the product for each nutrient, and nutrient goal of each nutrient associated with the user 102, respectively. The amount per servings of each nutrient corresponds to the quantity of nutrient consumption in each serving. The dosage value associated with each nutrient corresponds to a dosage value of the nutrient per serving. For example, a nutrient is depicted to be 'Ascorbic acid' with the amount of serving depicted to be '35 mg' and the dosage value by consuming the nutrient is exemplary depicted to be '14%' and the nutrient goal of the nutrient associated with the user 102 is depicted to be '17%'. Further, the user 102 may be redirected to the UI 300 based on selection of a button 348 rendered on the UI 340.

Figure 4A:
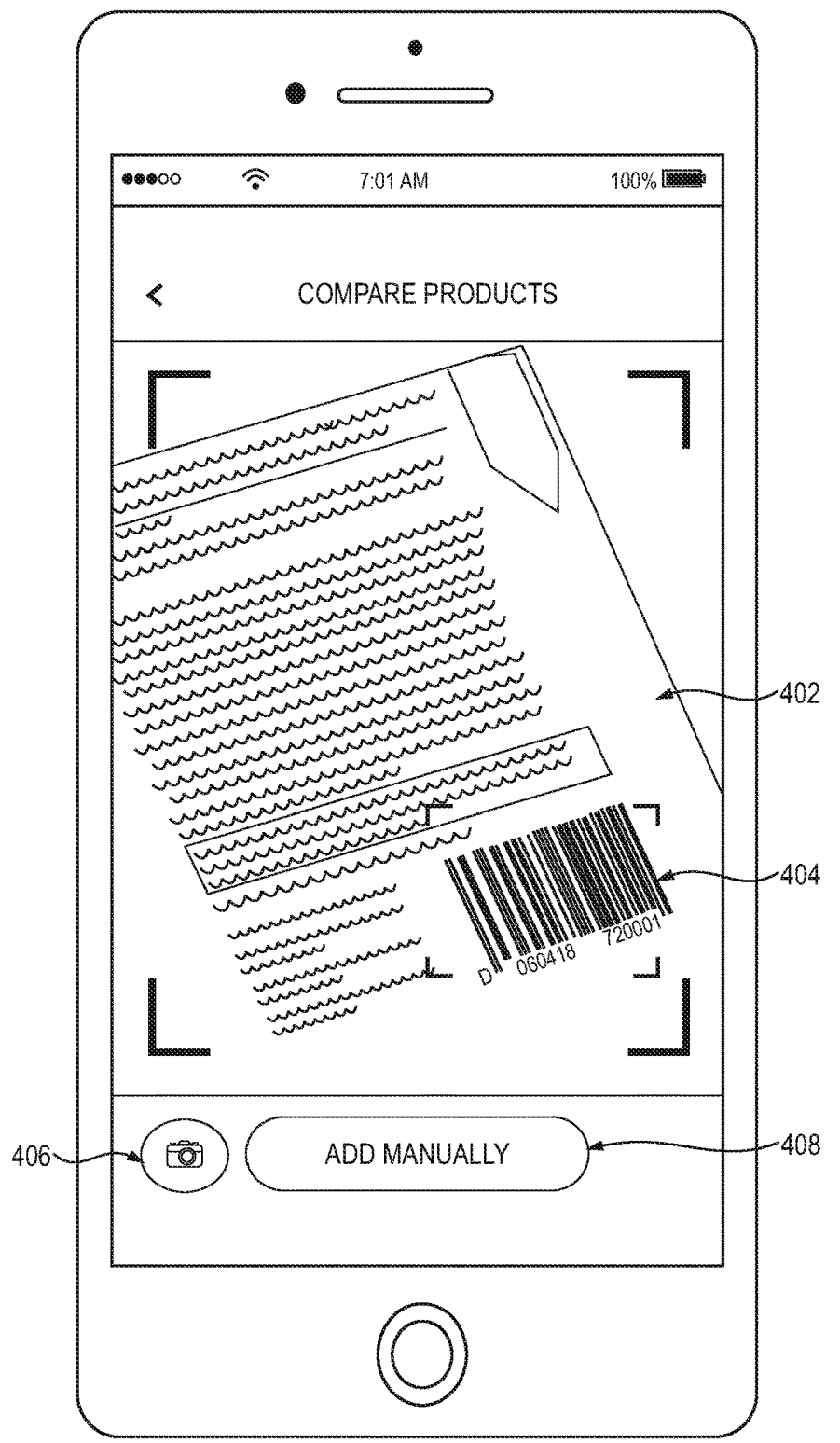
FIGS. 4A-4C, collectively, represent example representation of UIs displayed to the user depicting adding of a product to the list of products of FIG. 3, in accordance with an embodiment of the present disclosure.

Referring now to FIG. 4A, a representation of a UI 400 displayed to a user, depicting capturing of a product code is shown in accordance with an embodiment. The UI 400 is rendered by the health application 116 on the user device 104 based on user selection of an actionable icon 330 in the UI 300 of FIG. 3A. Further, the image capturing module of the user device 104 is triggered based on user input on the actionable icon 330 to capture the product label of the product. The UI 400 depicts a product label 402 that includes a product code 404 of the product. It should be noted that, in the UI 400 the product code 404 (exemplary depicted to be a 'barcode') is focused by the image capturing module by operating the user device 104. Further, the user 102 provides input on a button 406 to capture the product code 404 of the product. As such, the user 102 provides input on the button 406 to capture the product code 404. Thereafter, the product along with the dosage values is added to the list of products 316 in the nutrition diary 314 subsequent to decoding the product information appended to the product label 402 (shown as a barcode) as explained with reference to FIG. 2. In one embodiment, the product may also be added to the nutrition diary 314 by capturing the product label, such as the product label 402. In this case, the product is added to the list of products 316 based on determining the ingredients/nutrients on the product label 402.

Figure 4B:
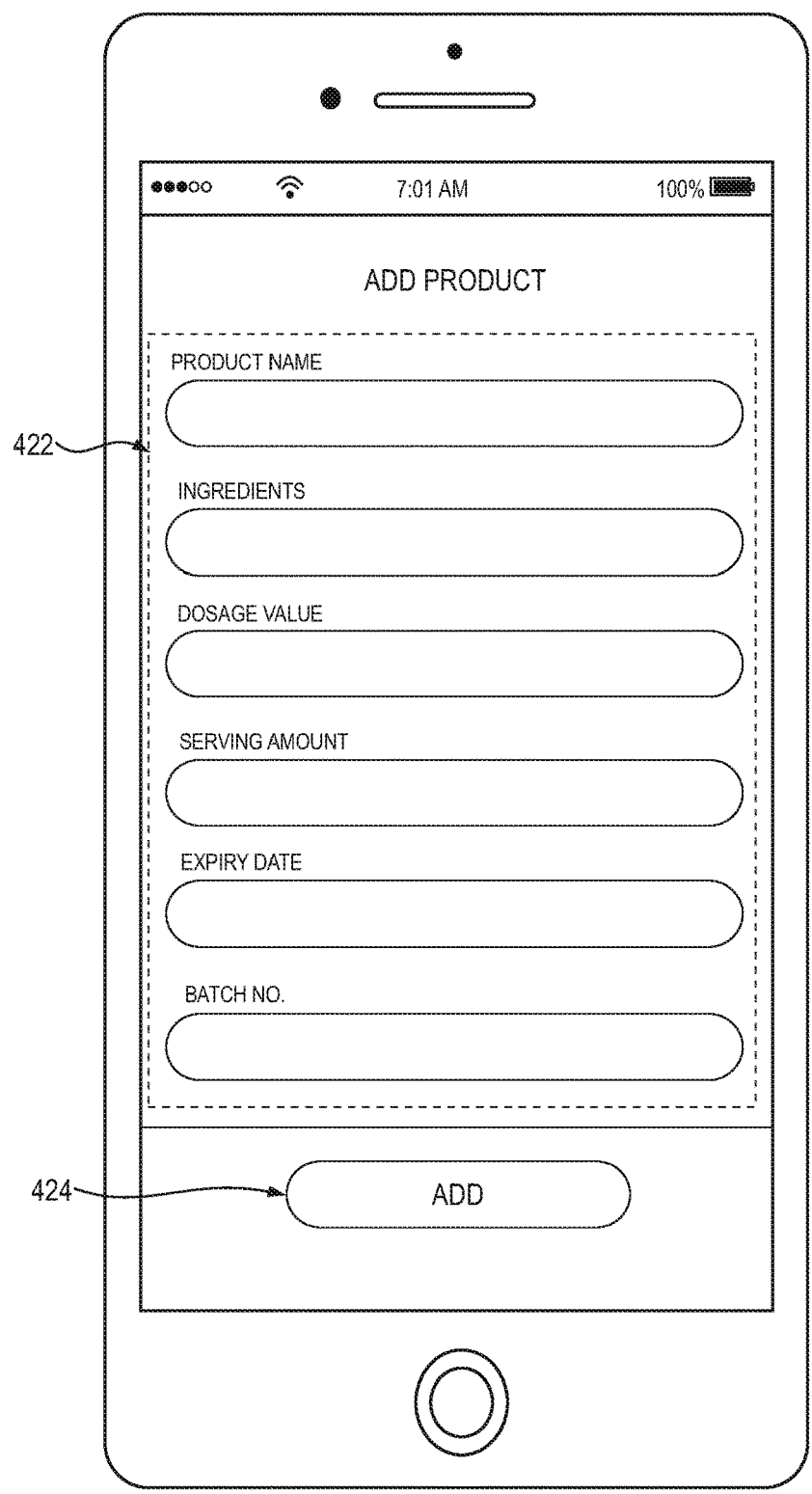

Further, the user 102 may also add the product to the nutrition diary 314 by manually entering the product details such as the product name, the ingredients, the serving amounts, the dosage values and the like. In this case, the user 102 may select a button 408 associated with the text 'ADD MANUALLY'. The user 102 is directed to a UI 420 to receive input related to the product details as mentioned above to add the product in the nutrition diary 314 (e.g., as shown in FIG. 4B). The UI 420 is depicted to include a plurality of information fields 422 to receive inputs related to a product which is being manually added by the user 102. Upon entering the product details, the user 102 selects a button 424 associated with the text 'ADD' to add the product to the nutrition diary 314.

Figure 4C:
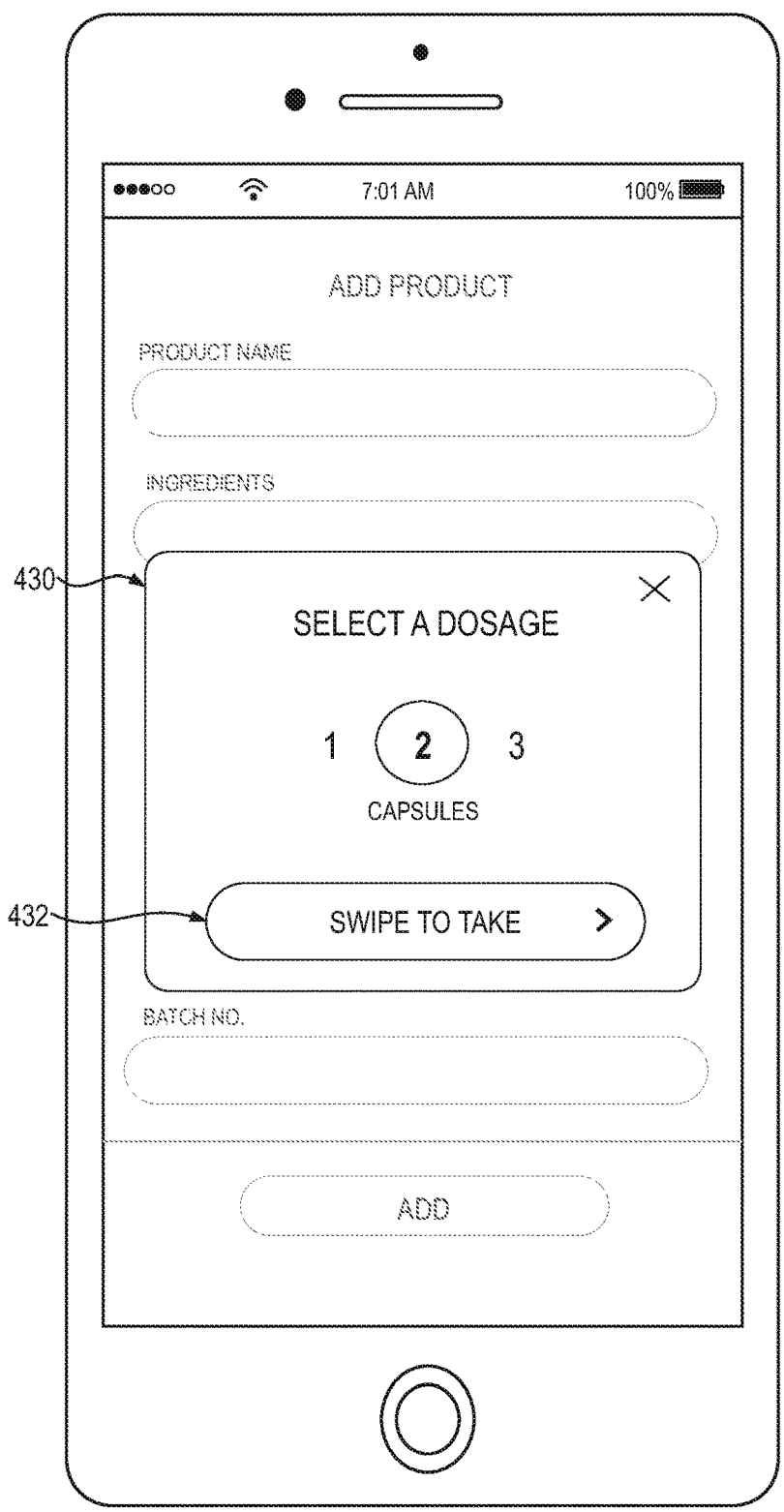

In one scenario, the user 102 may also add the product consumed that is not listed in the nutrition diary 314 by either scanning a product code, such as the product code 404 or by entering the product details manually by selecting the actionable icon 330. In this case, the user 102 may be prompted with a UI 430 in the health application 116 on the user device 104 to receive inputs on the dosage values consumed of that product (e.g., as shown in FIG. 4C). As such, the user 102 may select the dosage value consumed of the product (exemplary depicted to be '2 capsules'). Thereafter, the user 102 may swipe an actionable button 432 associated with the text 'SWIPE TO TAKE' to register consumption of the product. Further, the product consumed may be added to the nutrition diary 314 by the supplement management engine 220 for future use of the user 102.

Figure 5A:
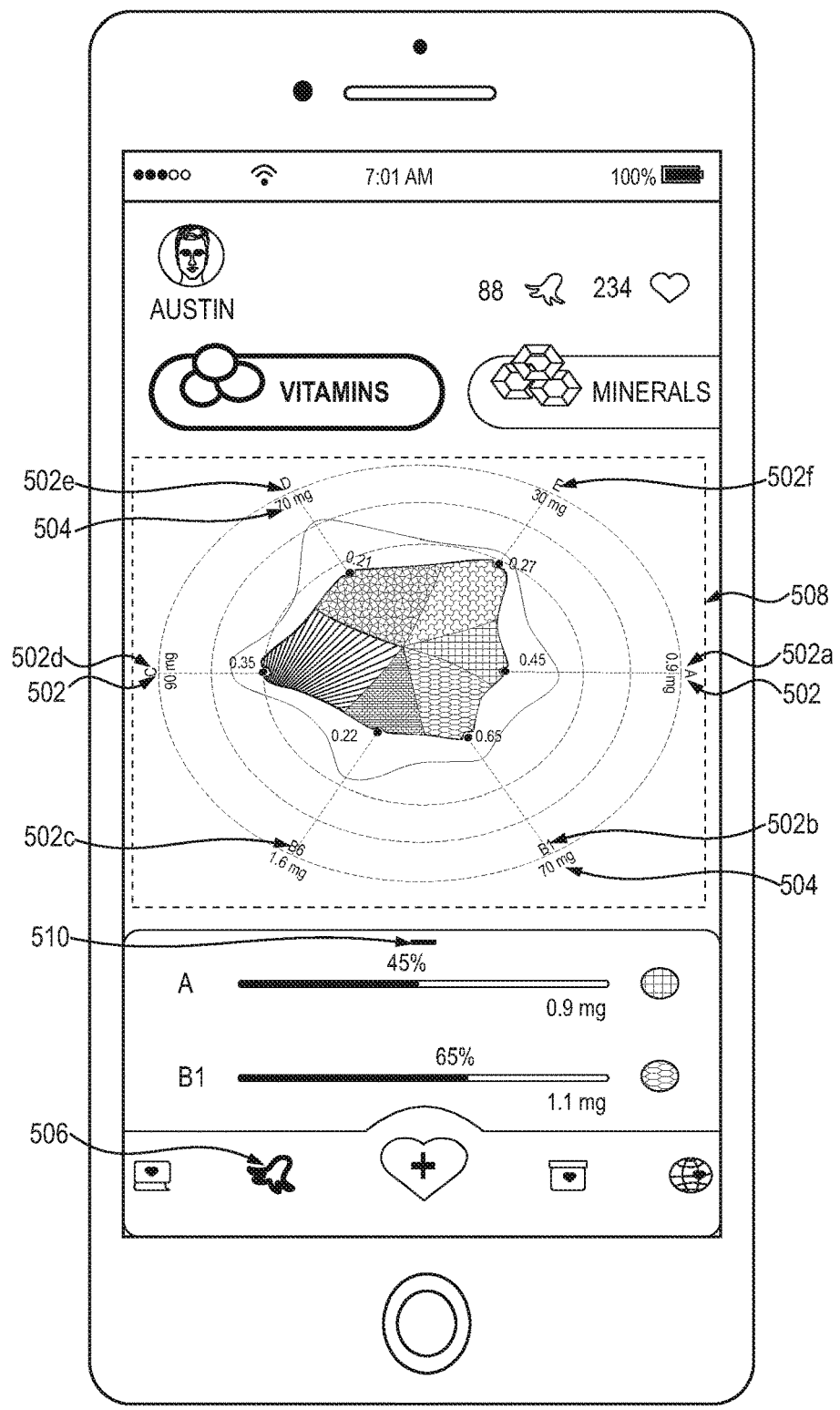
FIGS. 5A-5B collectively, represent example representation of UIs depicting a list of nutrients in the user profile of the user, in accordance with an embodiment of the present disclosure.
Figure 5B:
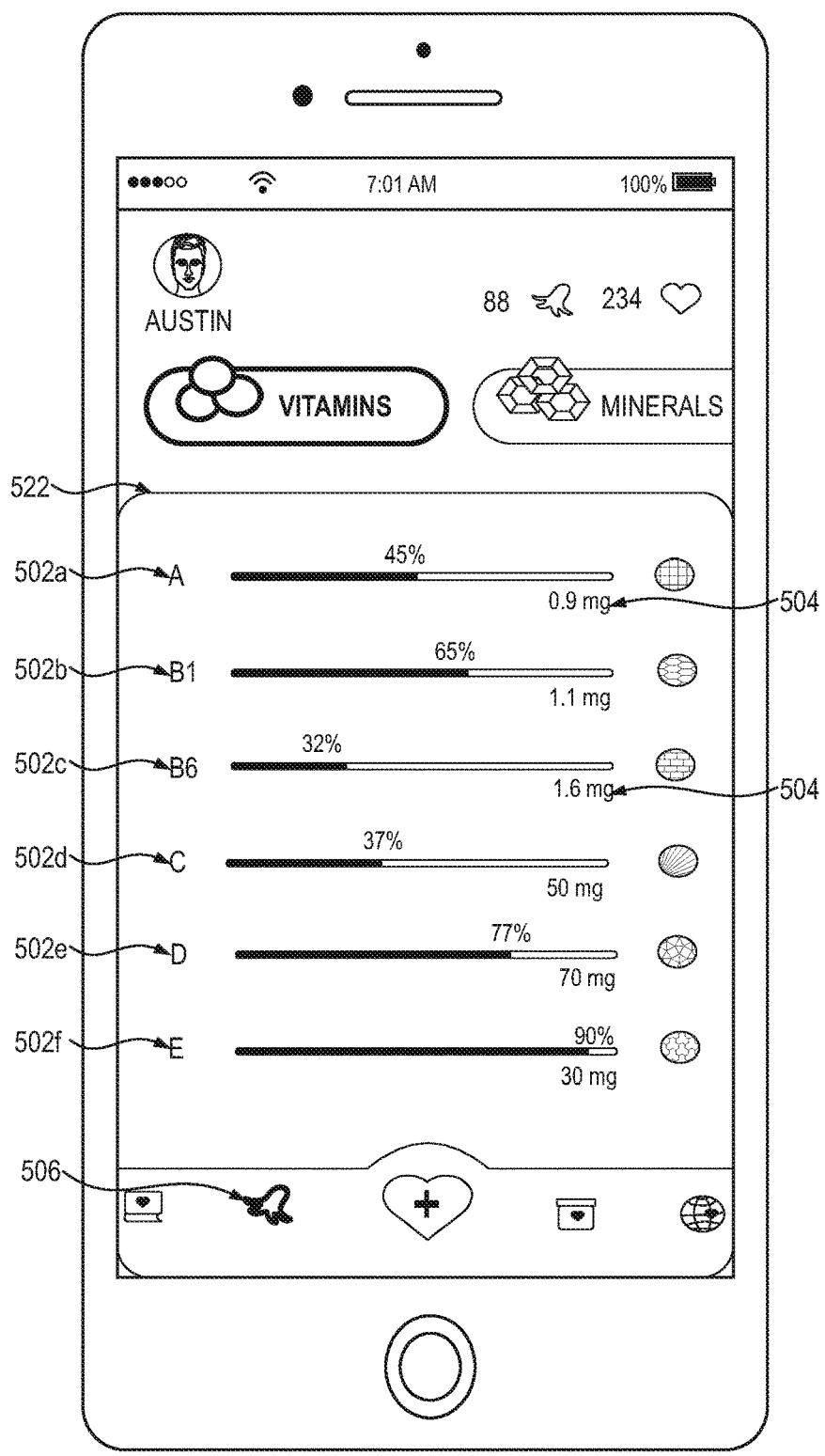

FIGS. 5A-5B collectively represent UIs depicting a list of nutrients in the user profile of the user 102, in accordance with an exemplary embodiment of the present disclosure.

Referring now to FIG. 5A, an example representation of a UI 500 depicting a list of nutrients on a radar chart is illustrated. The UI 500 is depicted based on selection of an actionable icon 506 by the user 102. The UI 500 depicts a list of nutrients 502a, 502b, 502c, 502d, 502e and 502f exemplary depicted as vitamins 'A', 'B1', 'B6', 'C', 'D' and 'E', respectively and corresponding dosage values 504 associated with each nutrient on a radar chart 508. The list of nutrients 502a-502f is collectively referred to as the list of nutrients 502. In particular, the UI 500 provides information to the user 102 related to the dosage values taken up to a certain time (e.g., in a day) along with the dosage values to be consumed for each nutrient to complete the nutrient goal. For instance, vitamin A represented on the radar chart 508 of the UI 500 is associated with the dosage value 504 exemplary depicted to be '0.9 mg' which corresponds to the nutrient goal of the vitamin A, and the amount of consumption of vitamin A is exemplary depicted to be 0.45. Further, the UI 500 is depicted to include a swipe up menu 510 that directs the user 102 to a UI 520. The UI 520 depicts the list of nutrients 502 in a data chart which is explained in detail with reference to FIG. 5B.

Referring now to FIG. 5B, an example representation of the UI 520 depicting the list of nutrients 502 on a data chart is illustrated. The UI 520 may be depicted subsequent to selection of the actionable icon 506 by the user 102. The UI 500 depicts the list of nutrients 502 and the dosage values 504 associated with each nutrient on a data chart 522. Particularly, the UI 520 depicts the amount of consumption of each nutrient 502 by the user 102 in percentages in the data chart 522 (e.g., as shown in FIG. 5B). For instance, vitamin A represented in the data chart 522 is associated with the dosage value 504 depicted to be '0.9 mg' which corresponds to the nutrient goal of vitamin A, and the amount of consumption of vitamin A is depicted to be '45%'. Further, the UIs 500 and 520 depicting the list of nutrients 502 may be customized by the user 102 in the health application 116. In an embodiment, the list of nutrients 502 plotted in the UI 500 or the UI 520 may be uniquely colored (not shown in Figures). As such, this form of representation of the nutrients 502 provides easy comprehension to the user 102 to compare and monitor the intake of the nutrients 502.

Figure 6:
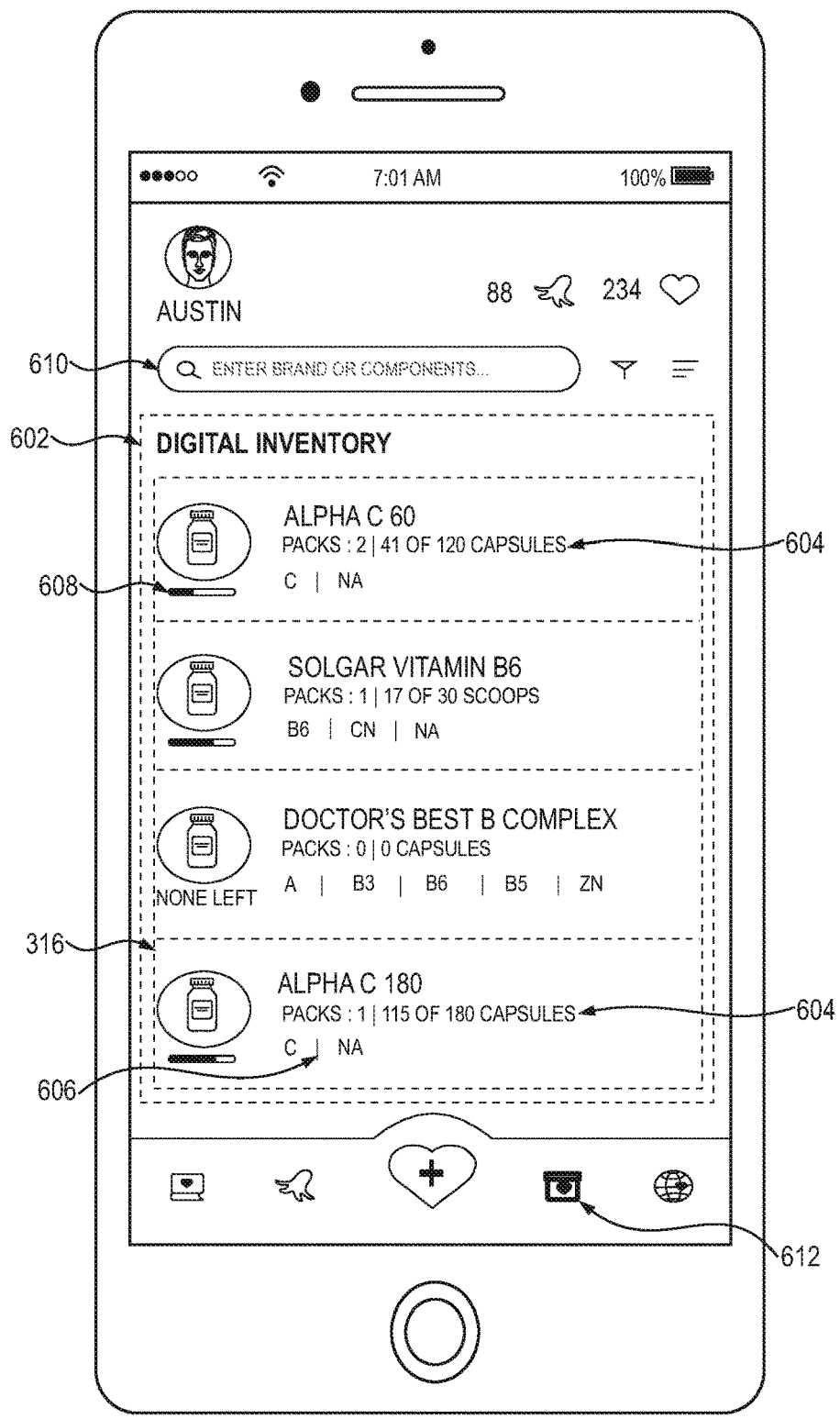
FIG. 6 illustrates an example representation of a UI displayed to the user depicting a digital inventory of the list of products of FIG. 3, in accordance with an embodiment of the present disclosure.

Referring now to FIG. 6, an example representation of a UI 600 depicting a digital inventory of the products owned by the user 102 is illustrated. The UI 600 renders multiple information fields related to a user, such as the user 102. The multiple information fields rendered are, for example, the username, the profile photo, the energy level indicator, and the reward points indicator as described with reference to FIG. 3A. The UI 600 depicts a digital inventory 602 based on a user selection of an actionable icon 612.

The digital inventory 602 of the UI 600 is depicted to include a list of products, such as the list of products 316 shown in FIG. 3A. The UI 600 further depicts the quantity 604 and ingredients 606 associated with each product in the digital inventory 602. In one embodiment, the UI 600 may also include expiry dates/days remaining for an expiry of a product, refill/subscription details and the like. Further, the quantity 604 associated with each product provides information on the contents remaining for each product (e.g., serving amounts, capsules). For example, a product from the list of products 316 (exemplary depicted to be 'Alpha C 60') in the UI 600 has 2 packs of Alpha C 60 product and number of servings remaining in the Alpha C 60 is depicted to be '41 of 120 capsules'.

It is noted that, based on the consumption of the at least one of the products 316 by the user 102, the quantity 604 of each product is simultaneously updated in the UI 600. Additionally, the UI 600 includes a product status bar 608 associated with each product (i.e., the products 316). The product status bar 608 may be a bar-like status bar that provides information on the quantity 604 associated with the product 316 owned by the user 102. Further, the product status bar 608 is also simultaneously updated based on consumption of the products 316 by the user 102. More specifically, the product status bar 608 depicts a quantity 604 remaining of each product (referenced by 'black portion') and the serving amounts consumed (referenced by 'white portion').

In an embodiment, the product 316 may be out of stock in the digital inventory 602. In this case, the product status bar 608 associated with the product 316 (e.g., 'Doctor's Best B complex') may be replaced by a status (exemplary depicted as 'NA') in the UI 600 (e.g., as shown in FIG. 6). In one embodiment, based on information of the quantity 604, the ingredients 606, and the product status bar 608 of the products 316, the server system 200 may either notify the user 102 or automatically order the products based on the user information. Therefore, the UI 600 enables the user 102 to track and manage the products 316 owned by the user 102 in the digital inventory 602. The UI 600 further includes a search field 610 for searching a particular nutrient or a product in the digital inventory 602 by providing inputs in the search field 610.

Figure 7:
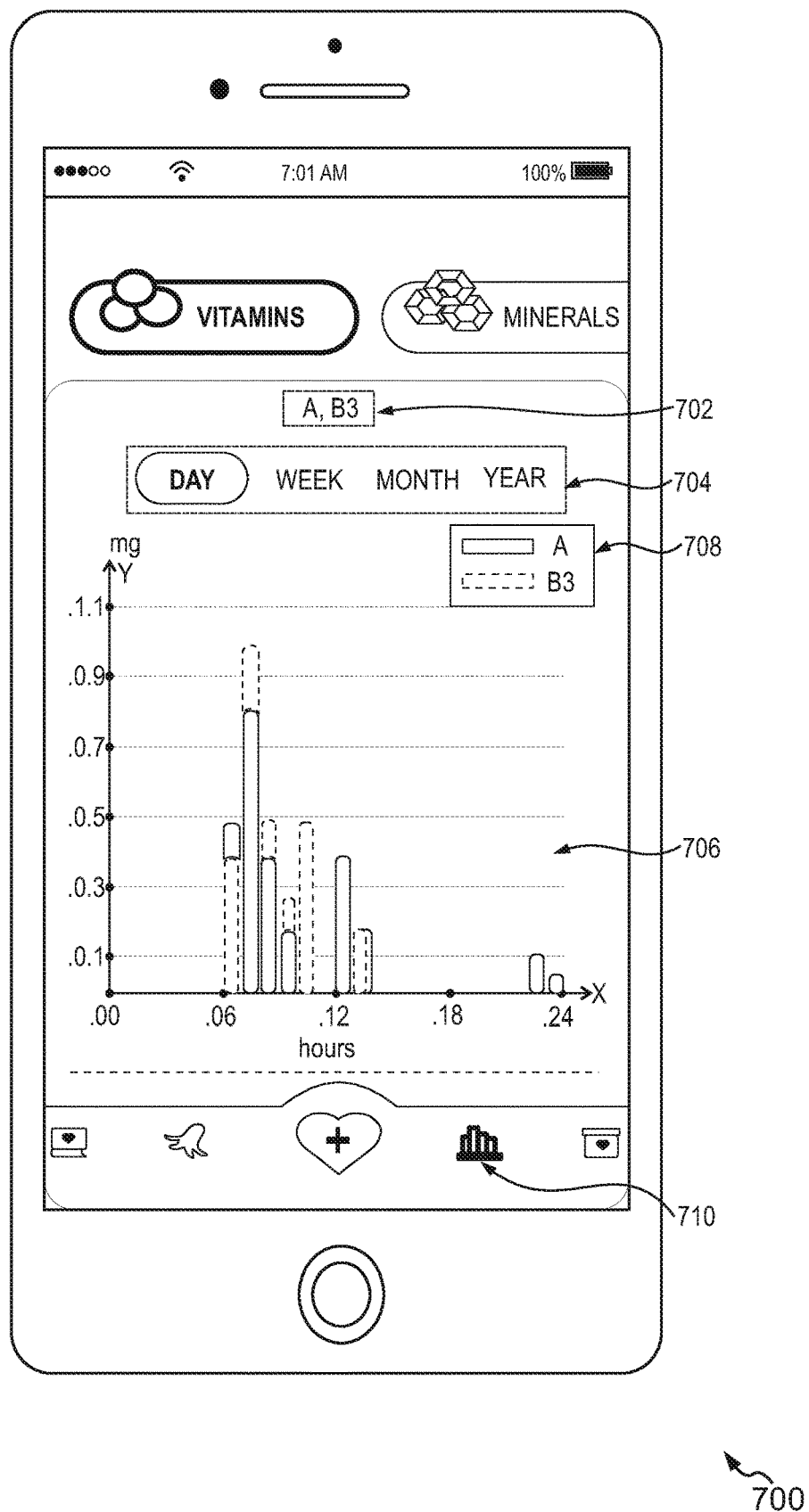
FIG. 7 illustrates an example representation of a UI displaying a nutrition log to the user, in accordance with an embodiment of the present disclosure.

Referring now to FIG. 7, an example representation of a UI 700 displaying a nutrition log is shown in accordance with an embodiment of the present disclosure. As shown in FIG. 7, the UI 700 is depicted to include the nutrient section 310 as described with reference to FIG. 3A. The UI 700 is displayed to the user 102, based on user selection of an actionable icon 710 in the health application 116.

In the illustrated example, the UI 700 is depicted to include nutrients 702 (exemplary depicted to be vitamin A and B3) and time interval 704 (exemplary depicted to be 'Day', 'Week', 'Month' and 'Year'). In an embodiment, the nutrients 702 may be selected by the user 102. Further, the depiction of only two nutrients (e.g., vitamins A and B3) is merely illustrative and should not be taken to limit the scope of the present disclosure.

The UI 700 is depicted to further include a nutrition log 706 (e.g., a 'bar graph'). The nutrition log 706 includes the dosage values of each nutrient represented on Y-axis and the time of nutrient intake represented on X-axis (e.g., as shown in FIG. 7). As such, the dosage value of each nutrient, such as the nutrients 702 and the time of nutrient intake is plotted on the nutrition log 706. For example, the X-axis of the nutrition log 706 is represented by 'hours' based on selection of the time interval 704 to be 'Day' (exemplary depicted to be a 'selection box' around the time interval 'Day' to indicate selection). The Y-axis of the nutrition log 706 is represented by milligrams (mg) and indicates the dosage values. Thus, vitamin A and B3 are plotted on the nutrition log 706 based on the intake of dosage of each nutrient (i.e., the nutrients 702) and the time of intake of the nutrients 702 by the user 102. It shall be noted that, the vitamin A is shown in continuous line and vitamin B3 is plotted in dashed line for illustrative purpose and should not be taken to limit the scope of the present disclosure (see, 708, of FIG. 7). As such, the nutrition log 706 allows the user 102 to compare the nutrient intake, monitor the dosage values of the nutrients 702 and the like.

In one embodiment, at least one product may be selected from a list of products, such as the list of products 316 of the digital inventory 602 and plotted in the nutrition log 706. In this form, the X-axis may be represented by time of product consumption and the Y-axis may be represented by amount of servings in the nutrition log 706. As such, the nutrition log 706 plotted for the products versus time allows the user 102 to compare the products consumed from the list of products 316 and monitor the nutrient intake as described above. In one form, the products or the nutrients (i.e., the nutrients 702) to be plotted in the nutrition log 706 may be selected by the user 102 based on providing inputs in the search field 610 of the UI 600. Additionally, the user 102 may provide inputs related to the nutrients in chemical form in the search field 610. As such, providing inputs in chemical form related to the nutrients 702 allows the user 102 to search for the ingredients at micronutrient level as explained with reference to FIG. 2. In an embodiment, the nutrition log 706 may be customized based on user selection of the nutrients, such as the nutrients 702 or the products from the digital inventory 602 in the health application 116. In other words, the server system 200 managing the health application 116 is configured to customize the nutrition log 706 based on user inputs related to the nutrients or the products in the health application 116.

In one embodiment, the nutrients 702 plotted on the nutrition log 706 may be uniquely colored (not shown in Figures) by the nutrition log engine 224 of the server system 200. As such, this form of representation of the nutrients 702 in the nutrition log 706 provides easy comprehension to the user 102 to compare and monitor the intake of the nutrients. Further, the user 102 may be provided with a notification on the user device 104 to remind the user 102 to consume a nutrient and complete the nutrient goal of the user 102 which is explained herein with reference to FIG. 8.

Figure 8:
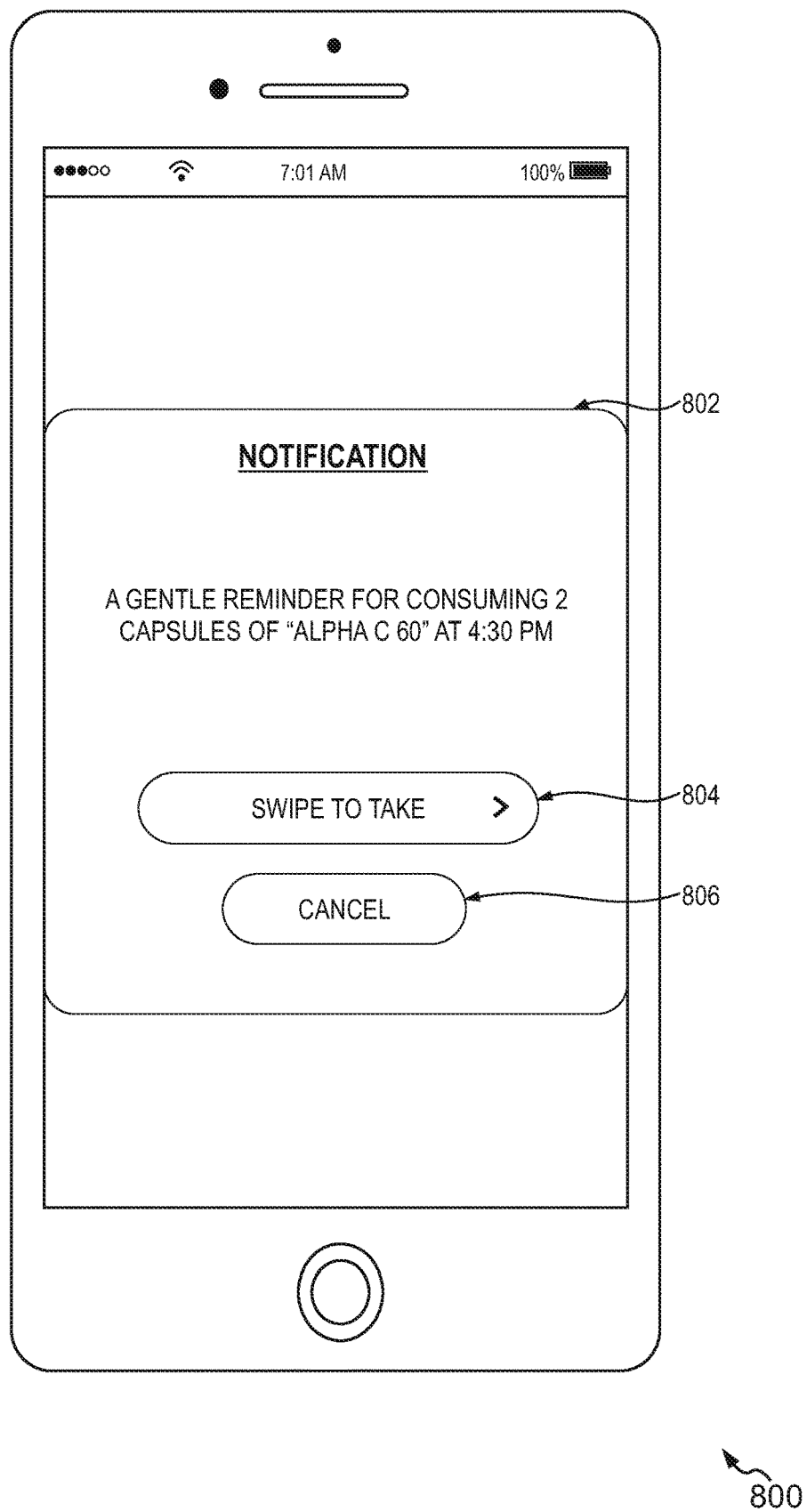
FIG. 8 illustrates an example representation of a UI displaying a notification related to nutrient intake to the user, in accordance with an embodiment of the present disclosure.

Referring now to FIG. 8, an example representation of a UI 800 displaying a notification for reminding the user to consume a nutrient is shown in accordance with an embodiment of the present disclosure. As shown in FIG. 8, the UI 800 is depicted to include a notification 802 displayed on a user device, such as the user device 104. For example, the notification 802 is depicted to include a reminder such as "A gentle reminder for consuming 2 capsules of "Alpha C 60" at 4:30 PM". Further, the user 102 may click on an actionable button 804 associated with the text 'SWIPE TO TAKE' displayed on the UI 800 to register the consumption of the product. As such, based on consumption of the product, the information related to the product will be updated in the nutrition diary 314 of the UI 300 and the digital inventory 602 of the UI 600. In one embodiment, the user 102 may be directed to the UI 300 upon clicking on the actionable button 804 by the user 102 thus enabling the user 102 to consume the product from the nutrition diary 314. In another embodiment, the user 102 may click on an actionable button 806 associated with the text 'CANCEL' that enables the user 102 to dismiss the notification displayed on the user device 104.

Figure 9:
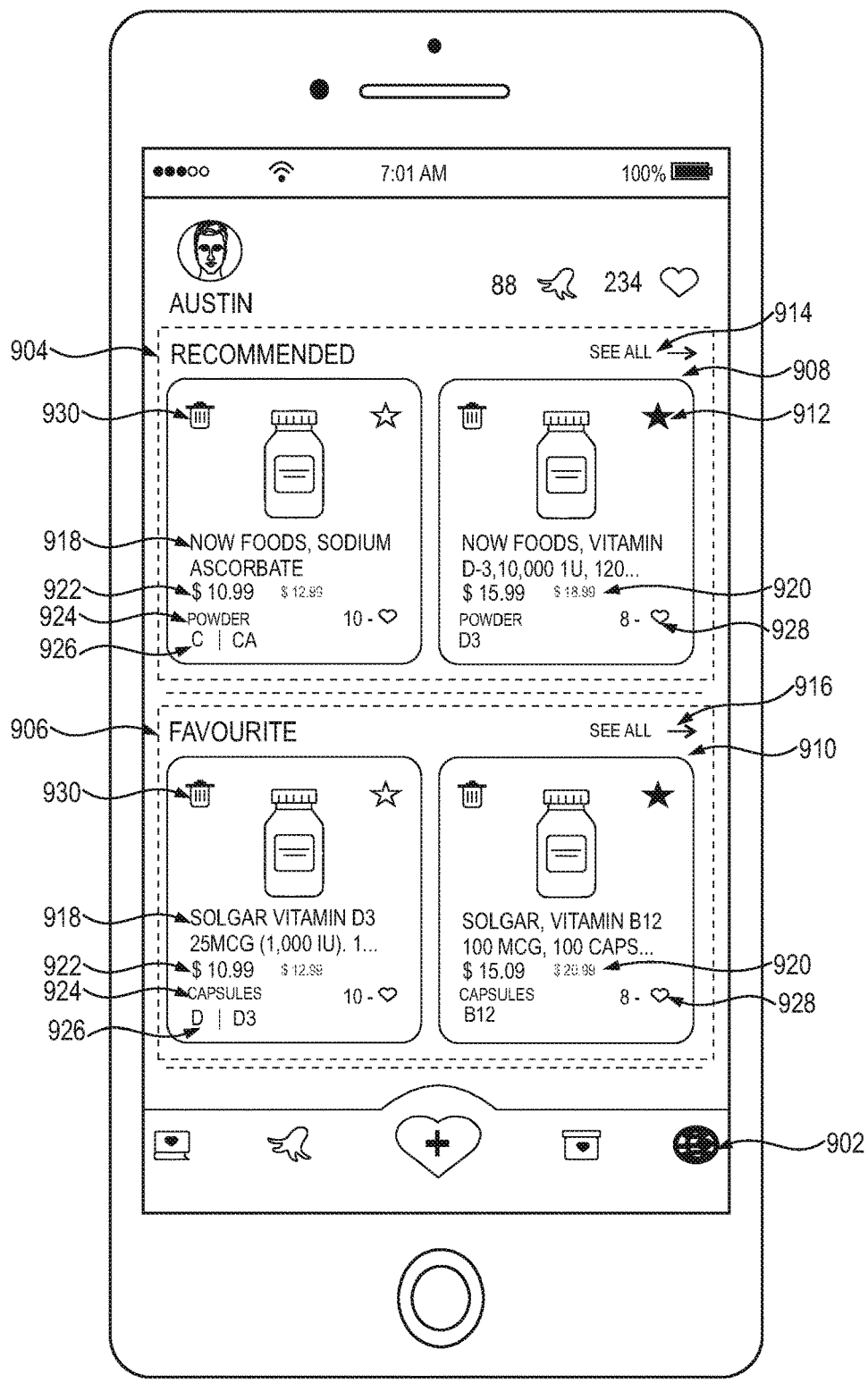
FIG. 9 illustrates an example representation of a UI depicting an online store associated with the health application, in accordance with an embodiment of the present disclosure.

FIG. 9 illustrates an example representation of a UI 900 depicting an online store associated with the health application 116, in accordance with an embodiment of the present disclosure. The UI 900 corresponds to an online store that offers a plurality of products to the user 102 for purchase. The UI 900 may be displayed to the user 102 on the user device 104 based on selection of an actionable icon 902 by the user 102. As shown in FIG. 9, the UI 900 is depicted to include multiple information fields of the user 102 such as the username 302, the profile photo 304, the energy level indicator 306, the reward points indicator 308 as described with reference to FIG. 3A. The UI 900 further includes a recommended products section 904 and a favorite products section 906.

The recommended products section 904 lists a plurality of products 908 recommended by a server system, such as the server system 200. The products 908 are recommended based on the user profile. In particular, the products 908 are recommended based at least on the products owned by the user 102, nutrients intake, nutrient consumption habits and the like. In one embodiment, the UI 900 may be depicted to include a search field (not shown in Figures) that facilitates the user 102 to search any product in an online store associated with the server system.

A favorite products section 906 in the UI 900 is depicted to include a list of products 910 which the user may mark as favorites. The products 910 in the section 906 are selected by the user 102 based on user input on an actionable button 912. In particular, the products 908 in the section 904 are added to the section 906 based on the user input on the actionable button 912. In an embodiment, the products 910 in the favorite products section 906 may be added by the server system 200 based on the products owned/used by the user 102 or the user information in the user profile. For illustrative purpose, only two products from the products 908 and 910 are depicted in the recommended products section 904 and the favorite products section 906 respectively. The products and the number of products displayed in the UI 900 should not be taken to limit the scope of the present disclosure.

Further, the UI 900 is depicted to include extended menus 914 and 916 associated with the text 'See all'. The extended menu 914 is associated with recommended products section 904 and the extended menu 916 is associated with the favorite products section 906. Upon selection of the extended menu 914 in the UI 900, the user 102 may be prompted with a UI (not shown in Figures) that depicts all the products of the plurality of products 908 of the recommended products section 904. Further, upon selection of the extended menu 916 in the UI 900, the user 102 may be prompted with a UI (not shown in Figures) that depicts all the products of the list of products 910 of the favorite products section 906.

The UI 900 further depicts information such as product name 918, product price 920, discounted product price 922, type of product 924, nutrients 926 and redeemable reward points 928 associated with each product (i.e., the products 908 and 910). The product price 920 of each product corresponds to the gross price of the product. The discounted product price 922 corresponds to the net price of the product. In one embodiment, the discounts on the product may be provided based on redemption of the reward points associated with the user 102. In another embodiment, discounts may also be provided based at least on frequency of purchase of the product by the user 102 and discounts by the merchants offering the product in the health application 116. In one scenario, the redeemable reward points 928 for purchase of the products 908 or 910 are determined by the server system 200. In another scenario, the user 102 may provide inputs on selection of the redeemable reward points 928 to the server system 200 while purchasing.

Further, the UI 900 is depicted to include an actionable button 930 that facilitates the user 102 to create a temporary list of products from the products 908 and the products 910 based on the user input on the actionable button 930. As such, the user 102 may be prompted with a UI (not shown in Figures) on the user device 104 that allows the user 102 to check the temporary list of products. In an embodiment, the user 102 may be directed to a UI (e.g., the UI 340) to view the product information of a product selected from the products 908 or 910. Further, the user 102 may select two or more products from the products 908 or 910 and request to compare the selected products in order to purchase a suitable product. This is explained in detail with reference to FIG. 10.

Figure 10:
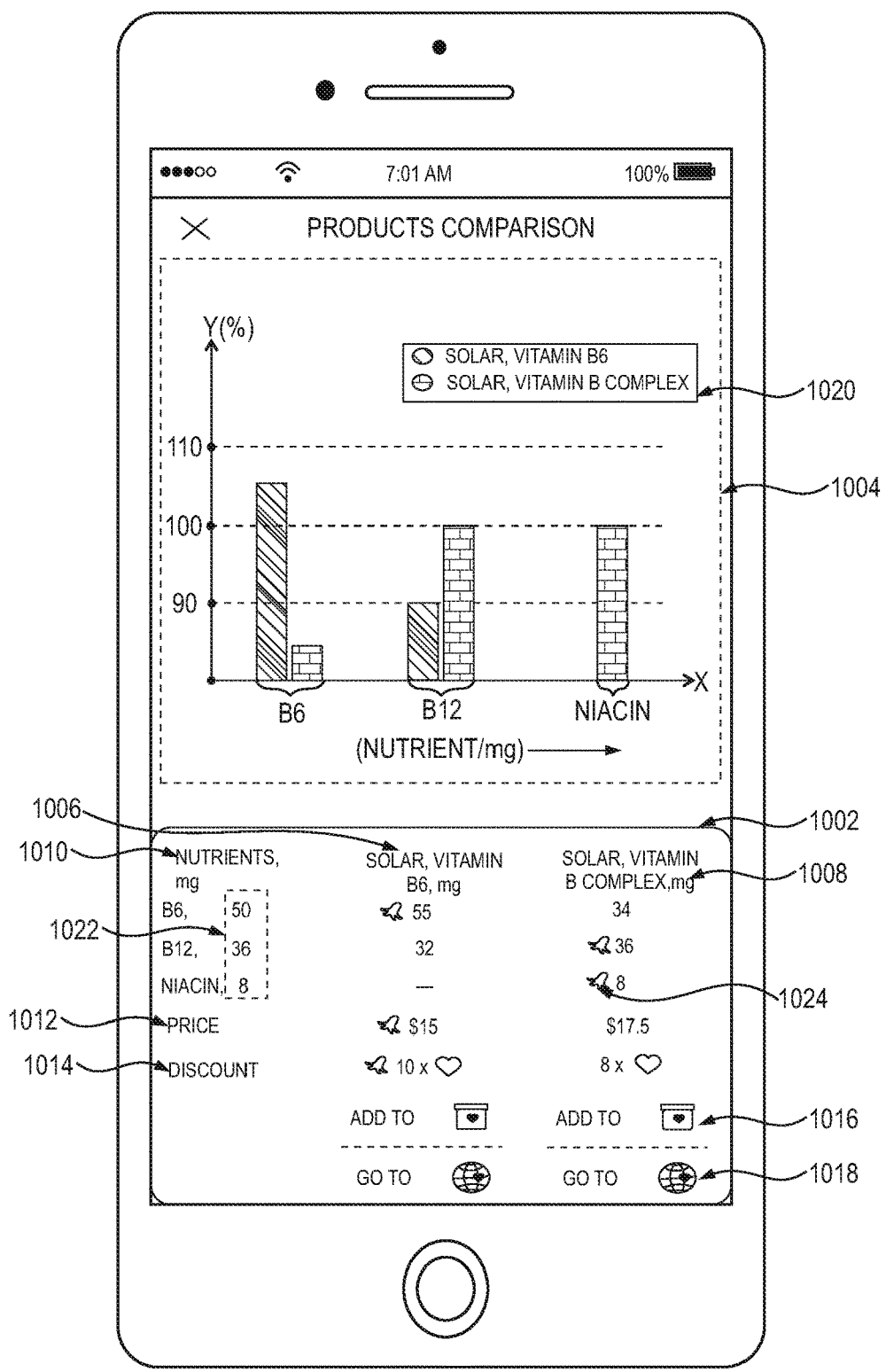
FIG. 10 illustrates an example representation of a UI displaying a comparison chart of two or more products to the user, in accordance with an embodiment of the present disclosure.

Referring now to FIG. 10, an example representation of a UI 1000 displaying a comparison chart of two or more products is shown in accordance with an embodiment of the present disclosure. As shown in FIG. 10, the UI 1000 is depicted to include a comparison table 1002 and a comparison graph 1004 (e.g., bar graph). The comparison table 1002 includes products 1006 and 1008 (exemplary depicted to be as 'Solar, Vitamin B6' and 'Solar, Vitamin B complex' respectively). For illustrative purpose, only two products (such as the products 1006 and 1008) are selected and described herein. Therefore, the products depicted in the UI 1000 should not be taken to limit the scope of the present disclosure.

The nutrients 1010 (exemplary depicted to be 'B6', 'B12' and 'Niacin') of the products 1006 and 1008 are listed in the UI 1000. In addition, the UI 1000 is depicted to include dosage values 1022 associated with the user 102 for each of the nutrients 1010. The dosage values 1022 of each of the nutrients 1010 correspond to the dosage value of the nutrient to be consumed by the user 102 based on the user profile. Further, the UI 1000 is depicted to include dosage values of each nutrient (i.e., the nutrients 1010) of the products 1006 and 1008. The comparison table 1002 provides comparison of each of the product (i.e., the products 1006 and 1008) on a nutrient level or ingredient level. For example, the dosage values of the nutrient 'B6' are depicted to be '55' and '34' for the products 1006 and 1008, respectively and the dosage value 1022 associated with the user 102 of the nutrient 'B6' is exemplary depicted to be '50'. It shall be noted that, the dosage values of the nutrients 1010 offered by the products 1006 and 1008 and the dosage values of the nutrients 1010 associated with the user 102 are represented in milligram (mg) (e.g., as shown in FIG. 10).

Further, the UI 1000 is depicted to include an indicator 1024 in the comparison table 1002. The indicator 1024 may be rendered on the UI 1000 by the server system 200 managing the health application 116. In particular, the indicator 1024 suggests the user a better product from among plurality of products being compared. In an embodiment, based on the user's requirement of a nutrient, the indicator 1024 may also suggest a better product having the highest percentage of the nutrient per serving. For example, the indicator 1024 is flagged to the nutrient 'B6' offered by the product 1006, since the dosage value of the nutrient 'B6' offered by the product 1006 meets the requirements of the dosage value of the nutrient 'B6' associated with the user 102. In other words, the indicator 1024 is flagged to the nutrient 'B6' offered by the product 1006 as the dosage value of the nutrient 'B6' offered by the product 1006 is greater than that of the product 1008. The comparison table 1002 of the UI 1000 is further depicted to include a product price 1012 and redeemable reward points 1014 of each product (i.e., the products 1006 and 1008). The product price 1012 is the gross product price and the redeemable reward points 1014 may be the reward points to avail discounts on the product price 1012 as described with reference to FIG. 9. For sake of brevity, the product price 1012 and the redeemable reward points 1014 are not explained herein in detail. Additionally, the indicator 1024 may also be flagged to the product price 1012 and the redeemable reward points 1014 as explained above.

Further, the dosage values associated with each nutrient (i.e., the nutrients 1010) and the dosage value of the nutrients 1010 associated with the user 102 for completing the at least one nutrient goal and plan are plotted on the comparison graph 1004. The comparison graph 1004 includes the nutrients 1010 and the dosage values each of the nutrients 1010 represented on the X-axis and the dosage value of each of the nutrients 1010 associated with the user 102 represented on the Y-axis (e.g., as shown in FIG. 10). More specifically, the Y-axis (i.e., dosage value of the nutrients 1010 associated with the user 102) is represented by percentage (%) and the X-axis (i.e., the dosage values of each of the nutrients 1010 offered by the products 1006 and 1008) is represented by nutrient/milligram (nutrient/mg). As such, the comparison graph 1004 is plotted by aligning same nutrients of the products 1006 and 1008 on the same line. It should be noted that, the comparison graph 1004 includes two bars, such as a first bar that is associated with the product 1006, a second bar that is associated with the product 1008 (see, 1020 of FIG. 10). For example, the dosage values of a nutrient (e.g., B6), offered by the products 1006 and 1008 are plotted using different bars in the comparison graph 1004. In an embodiment, the dosage values of each of the nutrients 1010 may be depicted inside the bars. Further, the vertical height of the bars along the Y-axis are plotted based on the dosage values of the nutrients 1010 offered by the products 1006 and 1008. Similarly, the dosage values of other nutrients (e.g., B12 and Niacin) are plotted in the comparison graph 1004. Thus, the UI 1000 allows the user 102 to compare the dosage values of the nutrients 1010 offered by the products 1006 and the 1008 along with the dosage values of each of the nutrients 1010 associated with the user 102. In one embodiment, each bar in the comparison graph 1004 may be uniquely colored (not shown in Figures). As such, this form of representation of the nutrients 1010 provides easy comprehension to the user 102 to compare and help the user 102 to decide the best suitable product for purchase. In an embodiment, the UI 1000 including the comparison table 1002 and the comparison graph 1004 may be customized by the user 102 or the server system 200 managing the health application 116.

In addition, the UI 1000 is depicted to include an option 1016 associated with the text 'ADD TO' for each product listed in the comparison table 1002. As such, the user 102 may select the option 1016 to add the product listed in the comparison table 1002 to a temporary list (i.e., add to cart) as described with reference to FIG. 9. Further, the UI 1000 is depicted to include an option 1018 associated with the text 'GO TO'. The user 102 is directed to the UI 900 based on selection of the option 1018 on the UI 1000.

Figure 11:
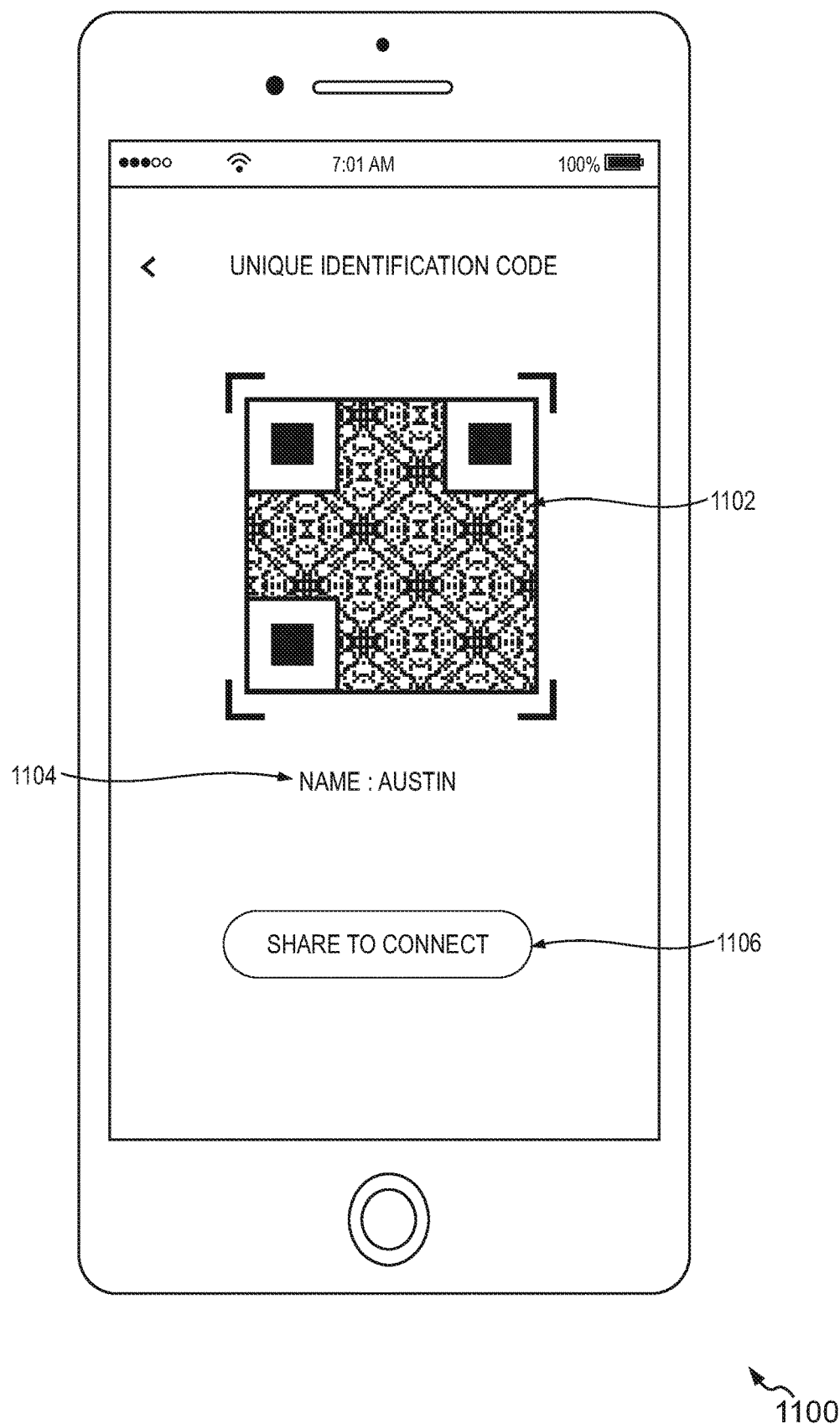
FIG. 11 illustrates an example representation of a UI displaying a unique identification code to the user, in accordance with an embodiment of the present disclosure.

Referring now to FIG. 11 an example representation of a UI 1100 depicting a user code is shown in accordance with an embodiment of the present disclosure. As shown in FIG. 11, the UI 1100 is depicted to include a user code 1102 (exemplary depicted to be a 'QR code'). In an embodiment, the user code 1102, associated with a user, such as the user 102, may be a barcode or a unique identification number. In another embodiment, the user code 1102 may be an application icon associated with the health application 116 (not shown in Figures). In this form, the application icon may be filled with bars corresponding to a unique barcode format and may exhibit same functionality of the user code 1102.

The user code 1102 is generated by the unique code generation engine 232 as described with reference to FIG. 2. The user code 1102 is appended with the user information related to the user 102 in the health application 116 as described with reference to FIGS. 2-10. Particularly, the user code 1102 maps the user 102 to the user profile. Further, the UI 1100 is depicted to include a username 1104 (i.e., the username 302 of FIG. 3A) of the user 102.

In one scenario, the user code 1102 is shared with registered users or non-registered users through one or more messaging channels. More specifically, the user 102 may click on an actionable button 1106 associated with the text 'SHARE TO CONNECT' to share the user code 1102. Upon clicking the button 1106, the user 102 may be prompted with a UI (not shown in Figures) that lists the one or more messaging channels on the user device 104. For instance, the one or more messaging channels may be a short messaging service (SMS), email, or any social media platform. Further, the information appended to the user code 1102 is periodically updated based on the user profile of the user 102. As such, the user code 1102 allows the user 102 to at least communicate and share the user profile to the registered users and the non-registered users of the health application 116. Further, the functionality of the user code 1102 is explained in detail with reference to FIG. 2. Therefore, for the sake of brevity, the functionality of the user code 1102 is not described in detail.

Figure 12:
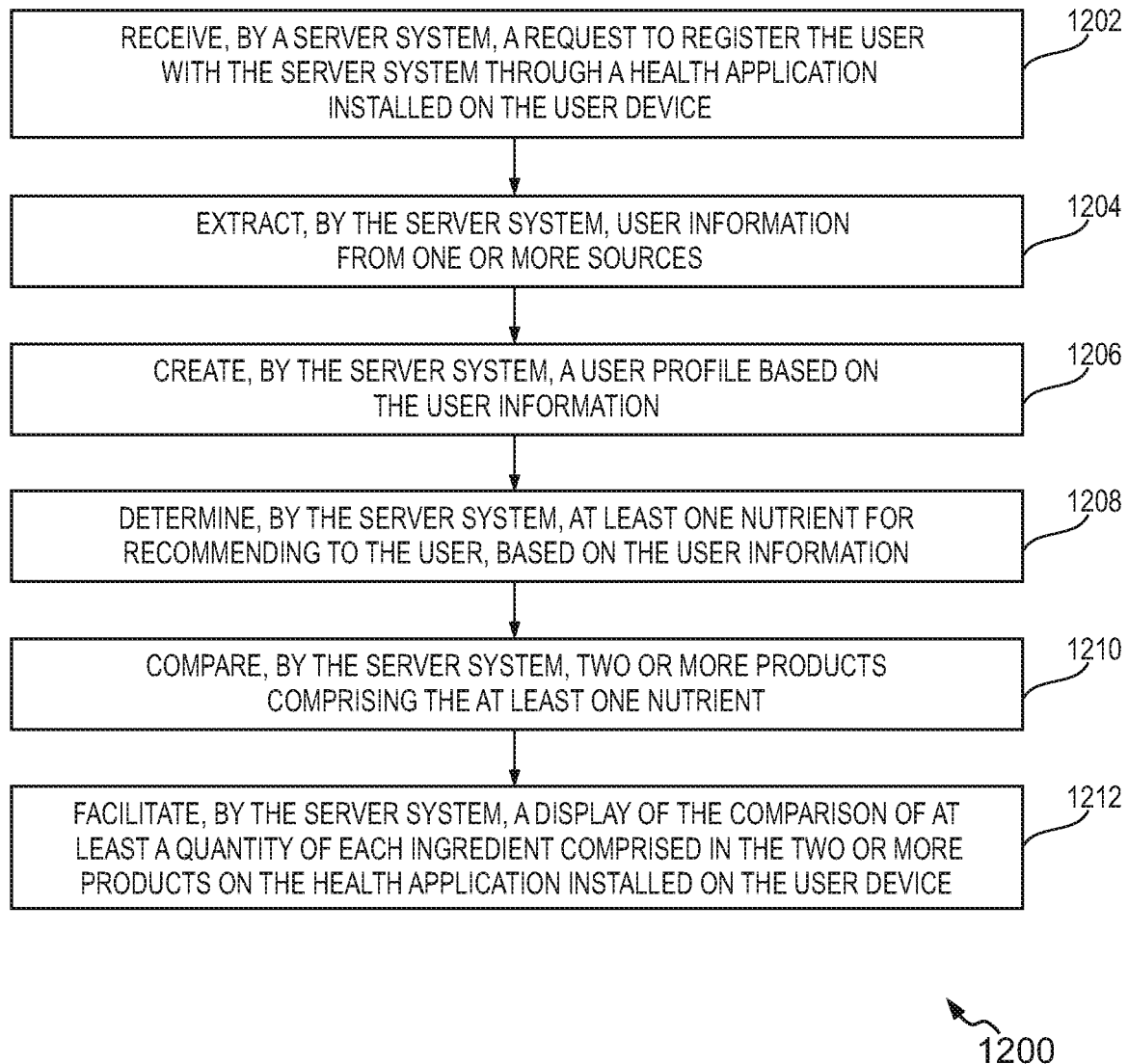
FIG. 12 illustrates a flow diagram of a method for managing nutrient intake of the user, in accordance with an embodiment of the present disclosure.

FIG. 12 illustrates a flow diagram of a method 1200 for managing nutrient intake of the user 102 associated with the user device 104, in accordance with an embodiment of the present disclosure. The method 1200 depicted in the flow diagram may be executed by, for example, the server system 200. Operations of the flow diagram of method 1200, and combinations of operation in the flow diagram of method 1200, may be implemented by, for example, hardware, firmware, a processor, circuitry, and/or a different device associated with the execution of software that includes one or more computer program instructions. It is noted that the operations of the method 1200 can be described and/or practiced by using a system other than these server systems. The method 1200 starts at operation 1202.

At operation 1202, the method 1200 includes receiving, by a server system, a request to register the user with the server system through the health application installed on the user device. The user 102 may provide information in the health application 116 communicably coupled to the server system 200 such as name, age, height, weight, health conditions and the like at the time of registration.

At operation 1204, the method 1200 includes extracting, by the server system, user information from one or more sources. The server system 200 accesses and retrieves information pertaining to the user 102 from the one or more sources such as the user device, one or more wearable devices associated with the user, one or more devices that track nutrient intake of the user, and external databases.

At operation 1206, the method 1200 includes creating, by the server system, a user profile based on the user information. The server system creates the user profile of the user in the health application indicating successful registration of the user with the server system.

At operation 1208, the method 1200 includes determining, by the server system, at least one nutrient for recommending to the user, based on the user information. The server system determines and recommends the at least one nutrient based on the information from the user 102 and the one or more sources. Further, the server system 200 may recommend the one or more products containing the at least one nutrient to the user 102.

At operation 1210, the method 1200 includes comparing, by the server system, two or more products including the at least one nutrient.

At operation 1212, the method 1200 includes facilitating, by the server system, a display of the comparison of at least a quantity of each ingredient included in the two or more products on the health application installed on the user device.

In another embodiment, the method performed by the server system includes determining one or more products from a plurality of products based on the determination of the at least one nutrient. The method includes facilitating display of the determined one or more products on the health application. The method includes receiving a user input indicating selection of the two or more products and comparing the two or more products including the at least one nutrient. At least quantities of each ingredient comprised in the two or more products are compared. The method includes determining at least one product from the two or more products for providing recommendation to the user based on the user profile and the comparison of the two or more products. The method further includes facilitating, on the health application, display of the comparison of at least a quantity of each ingredient included in the two or more products and the recommendation of the at least one product from the two or more products for the user.

In yet another embodiment, the method performed by the server system includes receiving a first signal indicating a consumption of dosage of one or more products. The method includes updating the user profile and calculating nutrients consumed by the user, based on the first signal. The method further includes facilitating a display of nutrients consumed by the user on the health application. The display includes source of each nutrient consumed by the user. The source of each nutrient is at least one of the one or more products.

In an embodiment, the method performed by the server system includes creating a unique identification of the user. The unique identification maps the user to the user profile.

The method also includes facilitating sharing of the unique identification of the user through one or more messaging channels to other users registered with the server system. The unique identification is configured to show engagement of the user with the health application to the other users. In another embodiment, the method performed by the server system includes creating, by the server system, a digital inventory that is displayed on the health application. The digital inventory includes listing of at least one or more products owned by the user and servings remaining of the one or more products. The method includes determining if serving in at least one product is less than a pre-determined threshold. In case it is determined that the serving in the at least one product is less than a pre-determined threshold, the method includes sending a second signal on the health application. The second signal indicates a reminder to refill the at least one product.

In another embodiment, the method performed by the server system includes determining a nutrients goal and a plan to achieve the nutrients goal for a user based on the user information. The plan to achieve the at least one nutrient goal includes a list of nutrients to be consumed by the user, a dosage of the one or more products by the user, and time and combination of consumption of the one or more products by the user. The method further includes sending at least one reminder to consume one or more products to achieve the nutrients goal according to the plan. The method further includes receiving a first signal indicating a consumption of a dosage of the one or more products and rewarding the user reward points holding monetary value on completion of the nutrients goal. In another embodiment, the method includes receiving a plurality of signals indicating consumption of dosage of one or more products at predetermined time intervals and updating at least one nutrient goal and a plan to achieve the at least one nutrient goal for a user based on the user information and the plurality of signals.

In an embodiment, the method includes receiving from a user a request for production of at least one product including one or more nutrients according to user's requirements. The method further includes identifying at least one vendor that is associated with the server system and is capable of manufacturing the at least one product. The method further includes sending, to the at least one vendor, the request for production of the at least one product comprising one or more nutrients according to the user's requirement.

Figure 13:
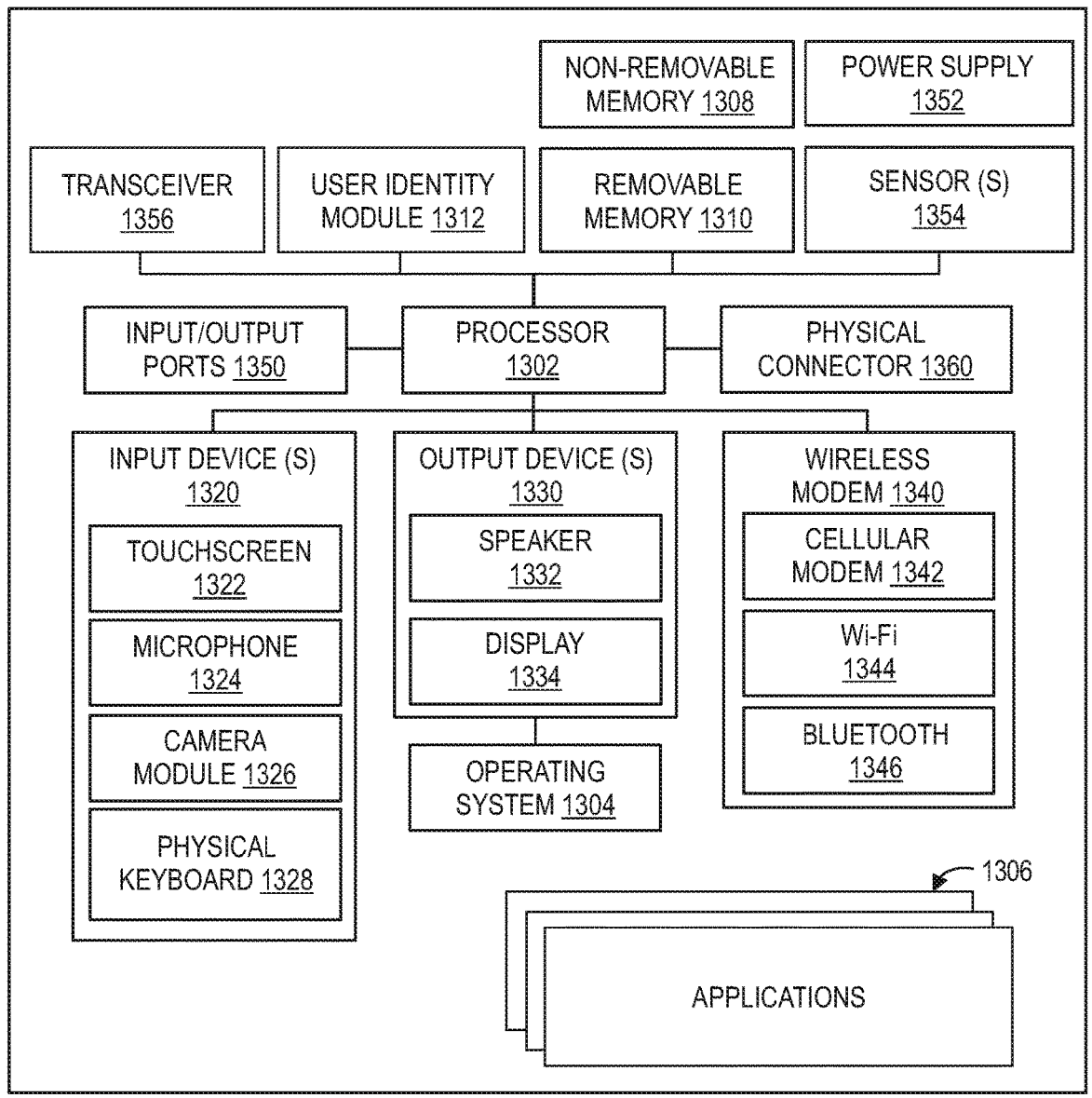
FIG. 13 is a simplified block diagram of an electronic device capable of implementing various embodiments of the present disclosure.

FIG. 13 shows a simplified block diagram of an electronic device 1300 capable of implementing various embodiments of the present disclosure. For example, the electronic device 1300 may correspond to the user device 104 of FIG. 1. The electronic device 1300 is depicted to include one or more applications 1306. For example, the one or more applications 1306 may include the health application 116 of FIG. 1. The health application 116 can be an instance of an application downloaded from the server system 200. One of the one or more applications 1306 installed on the electronic device 1300 are capable of communicating with a server system for managing nutrient intake of the user.

It should be understood that the electronic device 1300 as illustrated and hereinafter described is merely illustrative of one type of device and should not be taken to limit the scope of the embodiments. As such, it should be appreciated that at least some of the components described below in connection with the electronic device 1300 may be optional and thus in an embodiment may include more, less or different components than those described in connection with the embodiment of the FIG. 13. As such, among other examples, the electronic device 1300 could be any of a mobile electronic device, for example, cellular phones, tablet computers, laptops, mobile computers, personal digital assistants (PDAs), mobile televisions, mobile digital assistants, or any combination of the aforementioned, and other types of communication or multimedia devices.

The illustrated electronic device 1300 includes a controller or a processor 1302 (e.g., a signal processor, microprocessor, ASIC, or other control and processing logic circuitry) for performing such tasks as signal coding, data processing, image processing, input/output processing, power control, and/or other functions. An operating system 1304 controls the allocation and usage of the components of the electronic device 1300 and supports for one or more operations of the health application (see, the applications 1306), such as the health application 116 that implements one or more of the innovative features described herein. In addition, the applications 1306 may include common mobile computing applications (e.g., telephony applications, email applications, calendars, contact managers, web browsers, messaging applications) or any other computing application.

The illustrated electronic device 1300 includes one or more memory components, for example, a non-removable memory 1308 and/or removable memory 1310. The non-removable memory 1308 and/or the removable memory 1310 may be collectively known as a database in an embodiment. The non-removable memory 1308 can include RAM, ROM, flash memory, a hard disk, or other well-known memory storage technologies. The removable memory 1310 can include flash memory, smart cards, or a Subscriber Identity Module (SIM). The one or more memory components can be used for storing data and/or code for running the operating system 1304 and the applications 1306. The electronic device 1300 may further include a user identity module (UIM) 1312. The UIM 1312 may be a memory device having a processor built in. The UIM 1312 may include, for example, a subscriber identity module (SIM), a universal integrated circuit card (UICC), a universal subscriber identity module (USIM), a removable user identity module (R-UIM), or any other smart card. The UIM 1312 typically stores information elements related to a mobile subscriber. The UIM 1312 in form of the SIM card is well known in Global System for Mobile (GSM) communication systems, Code Division Multiple Access (CDMA) systems, or with third-generation (3G) wireless communication protocols such as Universal Mobile Telecommunications System (UMTS), CDMA9000, wideband CDMA (WCDMA) and time division-synchronous CDMA (TD-SCDMA), or with fourth-generation (4G) wireless communication protocols such as LTE (Long-Term Evolution).

The electronic device 1300 can support one or more input devices 1320 and one or more output devices 1330. Examples of the input devices 1320 may include, but are not limited to, a touch screen/a display screen 1322 (e.g., capable of capturing finger tap inputs, finger gesture inputs, multi-finger tap inputs, multi-finger gesture inputs, or keystroke inputs from a virtual keyboard or keypad), a microphone 1324 (e.g., capable of capturing voice input), a camera module 1326 (e.g., capable of capturing still picture images and/or video images) and a physical keyboard 1328. Examples of the output devices 1330 may include, but are not limited to, a speaker 1332 and a display 1334. Other possible output devices can include piezoelectric or other haptic output devices. Some devices can serve more than one input/output function. For example, the touch screen 1322 and the display 1334 can be combined into a single input/output device.

A wireless modem 1340 can be coupled to one or more antennas (not shown in the FIG. 13) and can support two-way communications between the processor 1302 and external devices, as is well understood in the art. The wireless modem 1340 is shown generically and can include, for example, a cellular modem 1342 for communicating at long range with the mobile communication network, a Wi-Fi compatible modem 1344 for communicating at short range with an external Bluetooth-equipped device or a local wireless data network or router, and/or a Bluetooth-compatible modem 1346. The wireless modem 1340 is typically configured for communication with one or more cellular networks, such as a GSM network for data and voice communications within a single cellular network, between cellular networks, or between the electronic device 1300 and a public switched telephone network (PSTN).

The electronic device 1300 can further include one or more input/output ports 1350, a power supply 1352, one or more sensors 1354 for example, an accelerometer, a gyroscope, a compass, or an infrared proximity sensor for detecting the orientation or motion of the electronic device 1300 and biometric sensors for scanning biometric identity of an authorized user, a transceiver 1356 (for wirelessly transmitting analog or digital signals) and/or a physical connector 1360, which can be a USB port, IEEE 1294 (FireWire) port, and/or RS-232 port. The illustrated components are not required or all-inclusive, as any of the components shown can be deleted and other components can be added.

The disclosed method with reference to FIG. 12, or one or more operations of the server system 200 may be implemented using software including computer-executable instructions stored on one or more computer-readable media (e.g., non-transitory computer-readable media, such as one or more optical media discs, volatile memory components (e.g., DRAM or SRAM), or nonvolatile memory or storage components (e.g., hard drives or solid-state nonvolatile memory components, such as Flash memory components)) and executed on a computer (e.g., any suitable computer, such as a laptop computer, net book, Web book, tablet computing device, smart phone, or other mobile computing device). Such software may be executed, for example, on a single local computer or in a network environment (e.g., via the Internet, a wide-area network, a local-area network, a remote web-based server, a client-server network (such as a cloud computing network), or other such network) using one or more network computers. Additionally, any of the intermediate or final data created and used during implementation of the disclosed methods or systems may also be stored on one or more computer-readable media (e.g., non-transitory computer-readable media) and are considered to be within the scope of the disclosed technology. Furthermore, any of the software-based embodiments may be uploaded, downloaded, or remotely accessed through a suitable communication means. Such suitable communication means includes, for example, the Internet, the World Wide Web, an intranet, software applications, cable (including fiber optic cable), magnetic communications, electromagnetic communications (including RF, microwave, and infrared communications), electronic communications, or other such communication means.

Although the invention has been described with reference to specific exemplary embodiments, it is noted that various modifications and changes may be made to these embodiments without departing from the broad spirit and scope of the invention. For example, the various operations, blocks, etc., described herein may be enabled and operated using hardware circuitry (for example, complementary metal oxide semiconductor (CMOS) based logic circuitry), firmware, software and/or any combination of hardware, firmware, and/or software (for example, embodied in a machine-readable medium). For example, the apparatuses and methods may be embodied using transistors, logic gates, and electrical circuits (for example, application specific integrated circuit (ASIC) circuitry and/or in Digital Signal Processor (DSP) circuitry).

Particularly, the server system 200 and its various components may be enabled using software and/or using transistors, logic gates, and electrical circuits (for example, integrated circuit circuitry such as ASIC circuitry). Various embodiments of the invention may include one or more computer programs stored or otherwise embodied on a computer-readable medium, wherein the computer programs are configured to cause a processor or computer to perform one or more operations. A computer-readable medium storing, embodying, or encoded with a computer program, or similar language, may be embodied as a tangible data storage device storing one or more software programs that are configured to cause a processor or computer to perform one or more operations. Such operations may be, for example, any of the steps or operations described herein. In some embodiments, the computer programs may be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (compact disc read only memory), CD-R (compact disc recordable), CD-R/W (compact disc rewritable), DVD (Digital Versatile Disc), BD (BLU-RAY® Disc), and semiconductor memories (such as mask ROM, PROM (programmable ROM), EPROM (erasable PROM), flash memory, RAM (random access memory), etc.). Additionally, a tangible data storage device may be embodied as one or more volatile memory devices, one or more non-volatile memory devices, and/or a combination of one or more volatile memory devices and non-volatile memory devices. In some embodiments, the computer programs may be provided to a computer using any type of transitory computer readable media. Examples of transitory computer readable media include electric signals, optical signals, and electromagnetic waves. Transitory computer readable media can provide the program to a computer via a wired communication line (e.g., electric wires, and optical fibers) or a wireless communication line.

Various embodiments of the disclosure, as discussed above, may be practiced with steps and/or operations in a different order, and/or with hardware elements in configurations, which are different than those which are disclosed. Therefore, although the disclosure has been described based upon these exemplary embodiments, it is noted that certain modifications, variations, and alternative constructions may be apparent and well within the spirit and scope of the disclosure.

Although various exemplary embodiments of the disclosure are described herein in a language specific to structural features and/or methodological acts, the subject matter defined in the appended claims is not necessarily limited to the specific features or acts described above. Rather, the specific features and acts described above are disclosed as exemplary forms of implementing the claims.

What is claimed is:

1. A method for managing micronutrient intake of a user associated with a user device, the method comprising:
receiving, by a server system, a request to register the user with the server system through a health application installed on the user device;
extracting, by the server system, user information from a plurality of sources, wherein extracting the user information comprises retrieving information related to the user from the plurality of sources and external databases, wherein the plurality of sources comprises the user device, one or more wearable devices associated with the user, and one or more nutrient trackers, and wherein the user information comprises information of: content of each micronutrient present in the user's body over a period of time, tracked diet, and other health metrics of the user;
creating, by the server system, a user profile based on the user information, wherein the user profile comprises information related to micronutrient consumption, dosage values, energy level based on amount of consumption of the micronutrients, consumption activity, one or more products possessed by the user, at least one micronutrient goal, and a micronutrition plan;
creating, by the server system, a unique identification of the user, wherein the unique identification maps the user to the user profile, and wherein the unique identification is a quick response code;
determining, by the server system, at least one micronutrient for recommending to the user, based on the user information;
comparing, by the server system, two or more products on an ingredient level comprising the at least one micronutrient by scanning a barcode corresponding to each product and capturing a product label of each product for comparison;
facilitating, by the server system, a display of the comparison of at least a quantity of each ingredient comprised in the two or more products on the health application installed on the user device;
determining, by the server system, a micronutrients goal and a plan to achieve the micronutrients goal for the user based on the user information, wherein the micronutrients goal comprises intake dosage required for each micronutrient of the at least one micronutrient determined based on the user information;
sending, by the server system, at least one reminder to the user device to consume one or more products to achieve the micronutrients goal according to the plan;
receiving, by the server system, a first signal indicating a consumption of a dosage of the one or more products, wherein the first signal includes at least a tactile input, a voice input, and a gesture input;
updating, by the server system, a quantity of each product of the one or more products in a digital inventory of the health application on the consumption of dosage of the one or more products;
tracking, by the server system, the contents of each supplement and recording a feedback on the products based on the user consumption of the products; and
automatically ordering, by the server system, one or more products based on the user consumption of the products.

2. The method as claimed in claim 1, further comprising:
determining, by the server system, one or more products from a plurality of products based on the determination of the at least one micronutrient, wherein at least one of the products of the two or more products is one of the one or more products;
facilitating, by the server system, display of the determined one or more products on the health application;
receiving, by the server system, a user input indicating selection of the two or more products;
comparing, by the server system, the two or more products comprising the at least one micronutrient, wherein at least quantities of each ingredient comprised in the two or more products are compared;
determining, by the server system, at least one product from the two or more products for providing a recommendation to the user based on the user profile and the comparison of the two or more products; and
facilitating, on the health application by the server system, the display of the comparison of the at least a quantity of each ingredient comprised in the two or more products and the recommendation of the at least one product from the two or more products for the user.

3. The method as claimed in claim 1, further comprising:
updating, by the server system, the user profile based on the first signal;
calculating, by the server system, micronutrients consumed by the user based on the first signal; and
facilitating, by the server system, a display of micronutrients consumed by the user on the health application, the display of micronutrients comprising source of each micronutrient consumed by the user, wherein the source of each micronutrient is at least one of the one or more products.

4. The method as claimed in claim 1, further comprising:
facilitating, by the server system, sharing of the unique identification of the user through one or more messaging channels to other users registered with the server system, wherein the unique identification is configured to show engagement of the user with the health application to the other users.

5. The method as claimed in claim 1, further comprising:
rewarding the user, by the server system, reward points holding monetary value on completion of the micronutrients goal.

6. The method as claimed in claim 5, wherein the plan to achieve the micronutrients goal comprises:
a list of micronutrients to be consumed by the user;
the dosage of the one or more products consumed by the user; and
time and combination of consumption of the one or more products by the user.

7. The method as claimed in claim 1, further comprising:
receiving, by the server system, a plurality of signals indicating consumption of dosage of one or more products at pre-determined time intervals; and
updating, by the server system, at least one micronutrient goal and a plan to achieve the at least one micronutrient goal for the user based on the user information and the plurality of signals.

8. The method as claimed in claim 1, further comprising:
creating, by the server system, the digital inventory that is displayed on the health application, wherein the digital inventory comprises of at least one or more products owned by the user and servings remaining of the one or more products;
determining, by the server system, whether serving in at least one product is less than a pre-determined threshold; and in case it is determined that the serving in the at least one product is less than a pre-determined threshold, sending, by the server system, a second signal on the health application, the second signal indicating a reminder to refill the at least one product.

9. The method as claimed in claim 1, the method further comprising:
receiving, from the user by the server system, a request for production of at least one product comprising one or more micronutrients according to the user's requirement;
identifying, by the server system, at least one vendor capable of manufacturing the at least one product, wherein the at least one vendor is associated with the server system; and
sending the at least one vendor, by the server system, the request for production of the at least one product comprising one or more micronutrients according to the user's requirement.

10. A server system for managing micronutrient intake of a user associated with a user device, the server system comprising:
a memory configured to store instructions; and
a processor configured to execute the instructions stored in the memory and thereby cause the server system to at least:
receive a request to register the user with the server system through a health application installed on the user device;
extract user information from a plurality of sources, wherein the extraction of the user information is performed by retrieving information related to the user from the plurality of sources and external databases, wherein the plurality of sources comprises the user device, one or more wearable devices associated with the user, and one or more nutrient trackers, and wherein the user information comprises information of: content of each micronutrient present in the user's body over a period of time, tracked diet, and other health metrics of the user;
create a user profile based on the user information, wherein the user profile comprises information related to micronutrient consumption, dosage values, energy level based on amount of consumption of the micronutrients, consumption activity, one or more products possessed by the user, at least one micronutrient goal, and a micronutrition plan;
create a unique identification of the user, wherein the unique identification maps the user to the user profile, and wherein the unique identification is a quick response code;
determine at least one micronutrient for recommending to the user, based on the user information;
compare two or more products on an ingredient level comprising the at least one micronutrient by scanning a barcode corresponding to each product and capturing a product label of each product for comparison;
facilitate a display of the comparison of at least a quantity of each ingredient comprised in the two or more products on the health application installed on the user device;
determine a micronutrients goal and a plan to achieve the micronutrients goal for the user based on the user information wherein the micronutrients goal comprises intake dosage required for each micronutrient of the at least one micronutrient determined based on the user information;
send at least one reminder to the user device to consume one or more products to achieve the micronutrients goal according to the plan;
receive a first signal indicating a consumption of a dosage of the one or more products wherein the first signal includes at least a tactile input, a voice input, and a gesture input;
update a quantity of each product of the one or more products in a digital inventory of the health application on the consumption of dosage of the one or more products;
track the contents of each supplement and record a feedback on the products based on the user consumption of the products; and
automatically order, one or more products based on the user consumption of the products.

11. The server system as claimed in claim 10, wherein the server system is further caused to:
determine one or more products from a plurality of products based on the determination of the at least one micronutrient, wherein at least one of the products of the two or more products is one of the one or more products;
facilitate display of the determined one or more products on the health application; receive a user input indicating selection of the two or more products;
compare the two or more products comprising the at least one micronutrient, wherein at least quantities of each ingredient comprised in the two or more products are compared;
determine at least one product from the two or more products for providing a recommendation to the user based on the user profile and the comparison of the two or more products; and
facilitate, on the health application, the display of the comparison of at least a quantity of the each ingredient comprised in the two or more products and the recommendation of the at least one product from the two or more products for the user.

12. The server system as claimed in claim 10, wherein the server system is further caused to:
update the user profile based on the first signal;
calculate micronutrients consumed by the user based on the first signal; and
facilitate a display of micronutrients consumed by the user on the health application, the display of micronutrients comprising source of each micronutrient consumed by the user, wherein the source of each micronutrient is at least one of the one or more products.

13. The server system as claimed in claim 10, wherein the server system is further caused to:
facilitate sharing of the unique identification of the user through one or more messaging channels to other users registered with the server system, and wherein the unique identification is configured to show engagement of the user with the health application to the other users.

14. The server system as claimed in claim 10, wherein the server system is further caused to:
reward the user with reward points holding monetary value on completion of the at least one micronutrient goal.

15. The server system as claimed in claim 10, wherein the server system is further caused to:

receive a plurality of signals indicating consumption of dosage of one or more products at pre-determined time intervals; and update at least one micronutrient goal and a plan to achieve the at least one micronutrient goal for the user based on the user information and the plurality of signals.

16. The server system as claimed in claim 10, wherein the server system is further caused to:

create the digital inventory that is displayed on the health application, wherein the digital inventory comprises of at least one or more products owned by the user and servings remaining of the one or more products;

determine whether serving in at least one product is less than a pre-determined threshold; and in case it is determined that the serving in the at least one product is less than a pre-determined threshold, send a second signal on the health application, the second signal indicating a reminder to refill the at least one product.

17. A system for managing micronutrient intake of a user associated with a user device, the system comprising:

a memory configured to store instructions; and a processor configured to execute the instructions stored in the memory and thereby cause the system to at least:

receive a request to register the user with the system through a health application installed on the user device;

extract user information from a plurality of sources, wherein the extraction of the user information is performed by retrieving information related to the user from the plurality of sources and external databases, wherein the plurality of sources comprises the user device, one or more wearable devices associated with the user, and one or more nutrient trackers, and wherein the user information comprises information of: content of each micronutrient present in the user's body over a period of time, tracked diet, and other health metrics of the user;

create a user profile based on the user information, wherein the user profile comprises information related to micronutrient consumption, dosage values, energy level based on amount of consumption of the micronutrients, consumption activity, one or more products possessed by the user, at least one micronutrient goal, and a micronutrition plan;

create a unique identification of the user, wherein the unique identification maps the user to the user profile, and wherein the unique identification is a quick response code;

determine at least one micronutrient for recommending to the user, based on the user information;

determine one or more products from a plurality of products based on the determination of the at least one micronutrient;

facilitate display of the determined one or more products on the health application;

receive a user input indicating selection of two or more products, wherein at least one of the products of the two or more products is one of the determined one or more products;

compare the two or more products comprising the at least one micronutrient by scanning a barcode corresponding to each product and capturing a product label of each product for comparison, wherein at least quantities of each ingredient comprised in the two or more products are compared;

determine at least one product from the two or more products for providing recommendation to the user based on the user profile and the comparison of the two or more products;

facilitate on the health application, display of the comparison of at least a quantity of each ingredient comprised in the two or more products and the recommendation of the at least one product from the two or more products for the user;

determine at least one micronutrient goal and a plan to achieve the at least one micronutrient goal for the user based on the user information, wherein the at least one micronutrient goal comprises intake dosage required for the at least one micronutrient determined based on the user information;

send at least one reminder to the user device to consume one or more products to achieve the at least one micronutrient goal according to the plan;

receive a first signal indicating a consumption of a dosage of the one or more products, wherein the first signal includes at least a tactile input, a voice input, and a gesture input;

update a quantity of each product of the one or more products in a digital inventory of the health application on the consumption of dosage of the one or more products;

track the contents of each supplement and record a feedback on the products based on the user consumption of the products;

automatically order, one or more products based on the user consumption of the products; and reward the user with reward points holding monetary value on completion of the at least one micronutrient goal, wherein the reward points are utilised to purchase the at least one product.

18. The system as claimed in claim 17, wherein the system is further caused to:

update the user profile based on the first signal;

calculate micronutrients consumed by the user based on the first signal; and facilitate a display of micronutrients consumed by the user on the health application, the display of micronutrients comprising source of each micronutrient consumed by the user, wherein the source of each micronutrient is at least one of the one or more products.

19. The system as claimed in claim 17, wherein the system is further caused to:

facilitate sharing of the unique identification of the user through one or more messaging channels to other users registered with the system, and wherein the unique identification is configured to show engagement of the user with the health application to the other users.

* * * * *